US010300000B2

(12) United States Patent
Goenka et al.

(10) Patent No.: US 10,300,000 B2
(45) Date of Patent: May 28, 2019

(54) INHIBITION OF MELANOGENESIS BY CHEMICALLY MODIFIED CURCUMINS

(71) Applicant: The Research Foundation for The State University of New York, Albany, NY (US)

(72) Inventors: Shilpi Goenka, Port Jefferson, NY (US); Sanford Simon, Stony Brook, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 15/702,122

(22) Filed: Sep. 12, 2017

(65) Prior Publication Data
US 2018/0071187 A1 Mar. 15, 2018

Related U.S. Application Data

(60) Provisional application No. 62/393,429, filed on Sep. 12, 2016.

(51) Int. Cl.
*A61K 31/165* (2006.01)
*A61K 8/42* (2006.01)
(Continued)

(52) U.S. Cl.
CPC .................. *A61K 8/42* (2013.01); *A61K 8/37* (2013.01); *A61Q 19/02* (2013.01); *A61K 31/167* (2013.01)

(58) Field of Classification Search
CPC .............................. A61K 31/216; A61K 31/165
(Continued)

(56) References Cited

U.S. PATENT DOCUMENTS

| 5,401,504 A | 3/1995 | Das et al. |
| 6,653,327 B2 | 11/2003 | Majeed et al. |

(Continued)

FOREIGN PATENT DOCUMENTS

| DE | 25 01 220 A1 | 7/1976 |
| JP | 2008 137914 A | 6/2008 |

(Continued)

OTHER PUBLICATIONS

Tu et al. "Curcumin inhibits melanogenesis in human melanocytes," Phytotherapy Research, 2012, vol. 26, pp. 174-179.*
(Continued)

*Primary Examiner* — Shengjun Wang
(74) *Attorney, Agent, or Firm* — Gary J. Gershik; Cooper & Dunham LLP

(57) ABSTRACT

The present invention provides a method of treating a subject afflicted with hyperpigmentation or of lightening the skin tone of a subject comprising administering to the subject an amount of a compound having the structure:

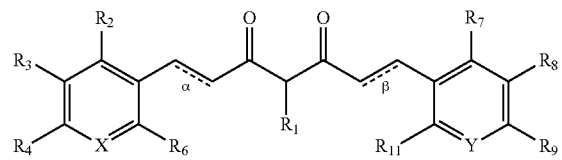

or a salt or ester thereof, so as to thereby treat the subject or lighten the skin tone of the subject.

20 Claims, 20 Drawing Sheets

(51) Int. Cl.
  *A61Q 19/02* (2006.01)
  *A61K 8/37* (2006.01)
  *A61K 31/167* (2006.01)
(58) Field of Classification Search
  USPC .............................................. 514/545, 563
  See application file for complete search history.

(56) References Cited

U.S. PATENT DOCUMENTS

| | | | |
|---|---|---|---|
| 7,579,486 | B2 | 8/2009 | Puerta et al. |
| 7,763,289 | B2 | 7/2010 | Bommarito |
| 8,236,852 | B2 | 8/2012 | Shih et al. |
| 9,187,406 | B2 | 11/2015 | Johnson et al. |
| 9,220,695 | B2 | 12/2015 | Golub et al. |
| 9,556,105 | B2 | 1/2017 | Johnson et al. |
| 9,675,576 | B2 | 6/2017 | Golub et al. |
| 2001/0051184 | A1 | 12/2001 | Heng |
| 2004/0253329 | A1 | 12/2004 | Mae et al. |
| 2005/0267221 | A1 | 12/2005 | Wellem et al. |
| 2006/0258752 | A1 | 11/2006 | Jagt et al. |
| 2006/0276536 | A1 | 12/2006 | Jagt et al. |
| 2007/0060644 | A1 | 3/2007 | Jagt et al. |
| 2007/0231334 | A1 | 10/2007 | Alibek et al. |
| 2008/0161391 | A1 | 7/2008 | Lee et al. |
| 2008/0200478 | A1 | 8/2008 | Robinson et al. |
| 2009/0018209 | A1 | 1/2009 | Arbiser |
| 2010/0010232 | A1 | 1/2010 | Neupert et al. |
| 2010/0152493 | A1 | 6/2010 | Shibata et al. |
| 2011/0044895 | A1 | 2/2011 | Berry et al. |
| 2011/0152382 | A1 | 6/2011 | Heng |
| 2012/0095051 | A1 | 4/2012 | Johnson et al. |
| 2015/0073021 | A1 | 3/2015 | Antonelli et al. |
| 2015/0150834 | A1 | 6/2015 | Golub et al. |

FOREIGN PATENT DOCUMENTS

| | | |
|---|---|---|
| KR | 2010-049929 | 5/2010 |
| WO | WO 2000/070949 A1 | 11/2000 |
| WO | WO 2013/059203 A1 | 4/2003 |
| WO | WO 2003/063793 A2 | 8/2003 |
| WO | WO 2003/088927 A2 | 10/2003 |
| WO | WO 2008/045534 A2 | 4/2008 |
| WO | WO 2008/048410 A2 | 4/2008 |
| WO | WO 2008/066151 A1 | 6/2008 |
| WO | WO 2008/085984 A1 | 7/2008 |
| WO | WO 2010/121007 A1 | 10/2010 |
| WO | WO 2010/132815 A1 | 11/2010 |
| WO | WO 2011/142795 A1 | 11/2011 |
| WO | WO 2014/005089 A2 | 1/2014 |
| WO | WO 2016/145159 A1 | 9/2016 |

OTHER PUBLICATIONS

Cai-Xia Tu, et al. (2012) Curcumin Inhibits Melanogenesis in Human Melanocytes. Phytother. Res. 26: 174-179.
Resmi Mustarichie, et al. (2013) In-Silico Study of Curcumin, Demethoxycurcumin and Xanthorrizol As Skin Whitening Agents. World J Pharm Sci. 1(3): 72-80.
Williams, A. Curcumin for Lightening Pigmented Skin. http://turmericsgold.com/conditions/curcumin-for-lightening-pigmented-skin/, accessed Oct. 6, 2017.
Majeed, M. et al. (2010) A randomized, double-blind, placebo-controlled, comparative study. Household and Personal Care Today—n Mar. 2010.
Smit, N. et al. (2009) The Hunt for Natural Skin Whitening Agents. Int. J. Mol. Sci. 10, 5326-5349.
Jiang, Y. et al. (2013) Synthesis and Biological Evaluation of Unsymmetrical Curcumin Analogues as Tyrosinase Inhibitors Molecules 2013, 18, 3948-3961.
Rattan, S.I. et al. (2007) Hormetic Prevention of Molecular Damage during Cellular Aging of Human Skin Fibroblasts and Keratinocytes. Ann. N.Y. Acad. Sci. 1100: 424-430.

International Search Report, dated Jul. 12, 2010 in connection with International Application No. PCT/2010/034971.
Written Opinion of the International Search Authority, dated Jul. 12, 2010 in connection with International Application No. PCT/2010/034971.
International Preliminary Report on Patentability Chapter I, dated Nov. 15, 2011 in connection with International Application No. PCT/2010/034971.
Office Action dated Dec. 16, 2014 in connection with U.S. Appl. No. 13/319,478.
Notice of Allowance dated Jul. 13, 2015 in connection with U.S. Appl. No. 13/319,478.
Notice of Allowance dated Oct. 11, 2016 in connection with U.S. Appl. No. 14/883,074.
Office Action dated Aug. 7, 2017 in connection with U.S. Appl. No. 15/383,735.
Extended European Search Report dated Oct. 18, 2012 in connection with European Application No. EP 10775624.9.
Communication Pursuant to Rules 70(2) and 70a(2) EPC dated Nov. 6, 2012 by the European Patent Office in connection with European Application No. EP 10775624.9.
Communication Pursuant to Art. 94(3) EPC dated Augsut 9, 2017 by the European Patent Office in connection with European Application No. EP 10775624.9.
International Search Report dated Jan. 17, 2013 in connection with International Application No. PCT/US2012/060437.
Written Opinion of the International Search Authority dated Jan. 17, 2013 in connection with International Application No. PCT/US2012/060437.
International Preliminary Report on Patentability Chapter I dated Apr. 22, 2014 in connection with International Application No. PCT/US2012/060437.
Office Action dated Mar. 12, 2015 in connection with U.S. Appl. No. 14/352,277.
Office Action dated Sep. 9, 2015 in connection with U.S. Appl. No. 14/352,277.
Final Office Action dated May 18, 2016 in connection with U.S. Appl. No. 14/352,277.
Office Action dated Jun. 20, 2017 in connection with U.S. Appl. No. 15/240,630.
Extended European Search Report dated Feb. 3, 2015 in connection with European application No. 12841310.1.
Office Action dated Feb. 11, 2016 in connection with European application No. 12841310.1.
International Search Report dated Feb. 14, 2014 in connection with International Application No. PCT/US2013/048710.
Written Opinion of the International Search Authority dated Feb. 14, 2014 in connection with International Application No. PCT/US2013/048710.
International Preliminary Report on Patentability Chapter I dated Feb. 14, 2014 in connection with International Application No. PCT/US2013/048710.
Notice of Allowance dated Aug. 13, 2015 in connection with U.S. Appl. No. 14/408,748.
Office Action dated Oct. 12, 2016 in connection with U.S. Appl. No. 14/950,033.
Extended European Search Report dated Jan. 8, 2016 in connection with European application No. 13808853.9.
Office Action dated Oct. 22, 2015 in connection with U.S. Appl. No. 14/478,886.
Final Office Action dated May 4, 2016 in connection with U.S. Appl. No. 14/478,886.
Office Action dated Nov. 7, 2016 in connection with U.S. Appl. No. 14/478,886.
International Search Report dated Aug. 18, 2016 in connection with International Application No. PCT/US2016/021723.
Written Opinion of the International Search Authority dated Aug. 18, 2016 in connection with International Application No. PCT/US2016/021723.
Pill-Hoon Bong (1999) "Spectral and photophysical behaviours of curcumin and curcuminoids." Bull. Korean Chem. Soc., vol. 21, No. 1, pp. 81-86.

(56) References Cited

OTHER PUBLICATIONS

Jankun et al. (2006) "Synthetic curcuminoids modulate the arachidonic acid metabolism of human platelet 12-lipoxygenase and reduce sprout formation of human endothelial cells", Molecular Cancer Therapeutics, vol. 5, No. 5, pp. 1371-1382.

Matthes et al. (1980) "Cytotoxic components of Zingiber Zerumbet, Curcuma Zedoaria and C. domestica", Phytochemistry, vol. 19, pp. 2643-2650.

Shao Wy et al. "Facile preparation of new unsymmetrical curcuma derivatives by solid-phase synthesis strategy" Tetrahedron Letters, vol. 47, No. 24, 2006, pp. 4085-4089.

Weber W.M. et al. "Activation of NFkappaB is inhibited by curcumin and related enones" Bioorganic & Medicinal Chemistry, vol. 14, No. 7, 2006, pp. 2450-2461.

Zhang et al. "Synthesis and cytotoxic activity of novel curcumin analogues" Chinese Chemical Letters, vol. 19, No. 3, 2008, pp. 281-285.

Third-Party Submission Under 37 CFR 1.290 dated Mar. 10, 2015 in connection with U.S. Appl. No. 14/352,277.

Antonelli, et al. "Inhibition of anthrax lethal factor by curcumin and chemically modified curcumin derivatives" J Enzyme Inhib Med Chem, 2014; 29(5): 663-669.

Lorencini, M et al. (2009) "Changes in MMPs and inflammatory cells in experimental gingivitis" Histol Histopathol 24, 157-166 (Summmary).

Bin Bao et al. (2011) "Anti-Tumor Activity of a Novel Compound-CDF Is Mediated by Regulating miR-21, miR-200, and PTEN in Pancreatic Cancer" PLOS ONE, 6, e17850.

Botchkina, et al. (2010) "New-generation taxoid SB-T-1214 inhibits stem cell-related gene expression in 3D cancer spheroids induced by purified colon tumor-initiating cells" Molecular Cancer, 9, 192.

Botchkina, et al. (2013) "Prostate Cancer Stem Cell-Targeted Efficacy of a New-Generation Taxoid, SBT-1214 and Novel Polyenolic Zinc-Binding Curcuminoid, CMC2.24" PLOS ONE, 9, e69884.

Zhou et al. (2008) "NF-kappaB pathway inhibitprs prefeentially inhibit breast cancer stem-like cells" Breast Cancer Res Treat, 111, 419.

Venkatesan, N. et al. (2007) Protection from acute and chronic lung diseases by curcumin. Adv Exp Med Biol, 595, pp. 379-405.

Bansal, S. et al. (2010) Curcumin alone and in combination with augmentin protects against pulmonary inflammation and acute lung injury generated during Klebsiella pneumoniae B5055-induced lung infection in BALB/c mice. J Med Microbiol, 59 (Pt 4), pp. 429-437.

Bonnans C. et al. (2007) Lipid mediators as agonists for the resolution of acute lung inflammation and injury. Am J Respir Cell Mol Biol, 36(2), pp. 201-205.

Seki, H. et al. (2010) the anti-inflammatory and proresolving mediator resolvin El protects mice from bacterial pneumonia and acutre lung injury. J Immunol, 184(2), pp. 836-843.

Communication Pursuant to Art. 94 (3) EPC dated Jan. 4, 2018 by the European Patent Office in connection with European Application No. EP 10775624.9.

Office Action dated Apr. 15, 2017 in connection with European application No. 13808853.9.

International Preliminary Report on Patentability Chapter 1 dated Sep. 12, 2017 in connection with international Application No. PCT/US2016/021723.

Office Action dated Feb. 6, 2018 in connection with U.S. Appl. No. 15/556,441.

Office Action dated Mar. 12, 2018 in connection with U.S. Appl. No. 15/702,122.

Berger, A.L. et al. (2005) Curcumin Stimulates Cystic Fibrosis Transmembrane Conductance Regulator Cl—Channel Activity, J. Biol. Chem.,280, 7, 5221-5226.

CAS Registry No. RN 1030857-94-3 (2008).

CAS Registry No. RN 1030860-08-2 (2008).

CAS Registry No. RN 194875-80-6 (1985).

Ito, N. et al. (2002) A medium-term rat liver bioassay for rapid in vivo detection of cacinogenic potential of chemicals. Cancer Sci, 94, 1, 3-8.

* cited by examiner

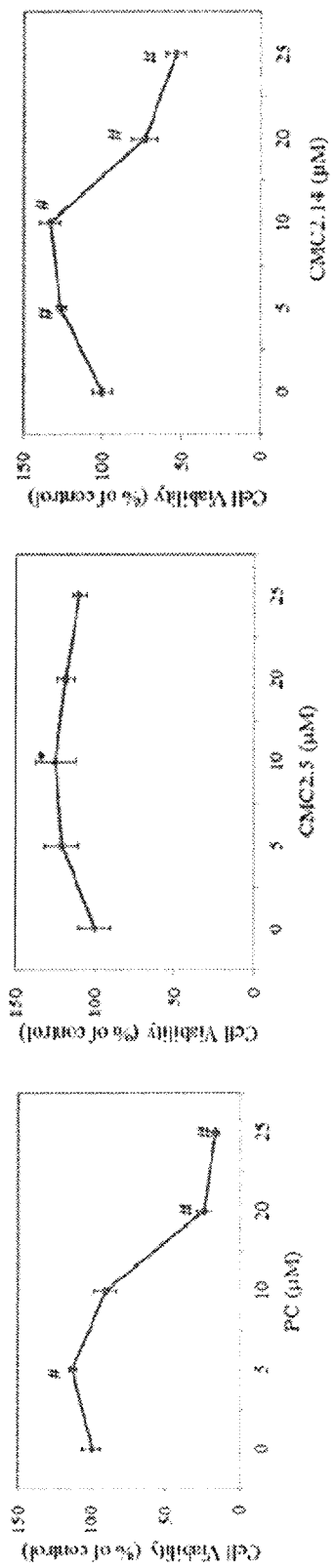

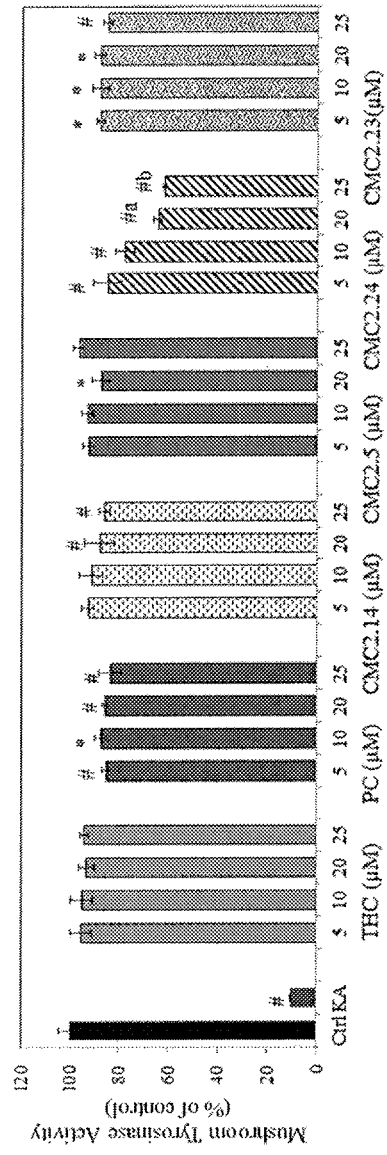
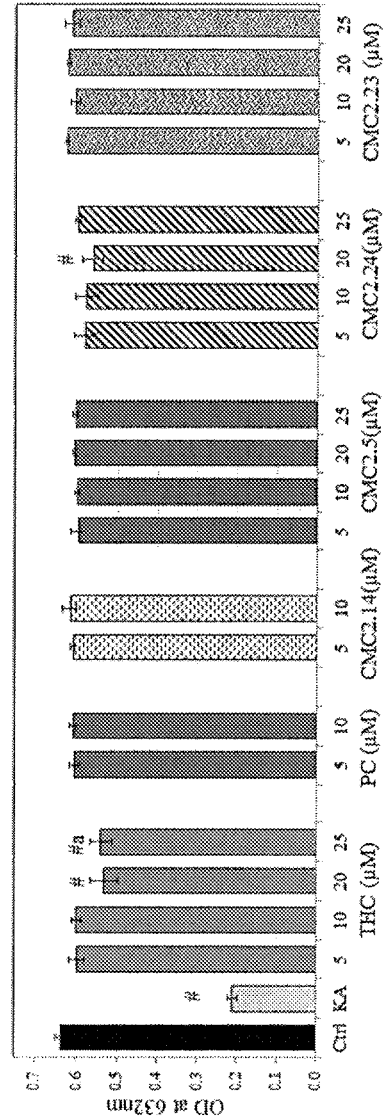
Fig. 3A
Fig. 3B

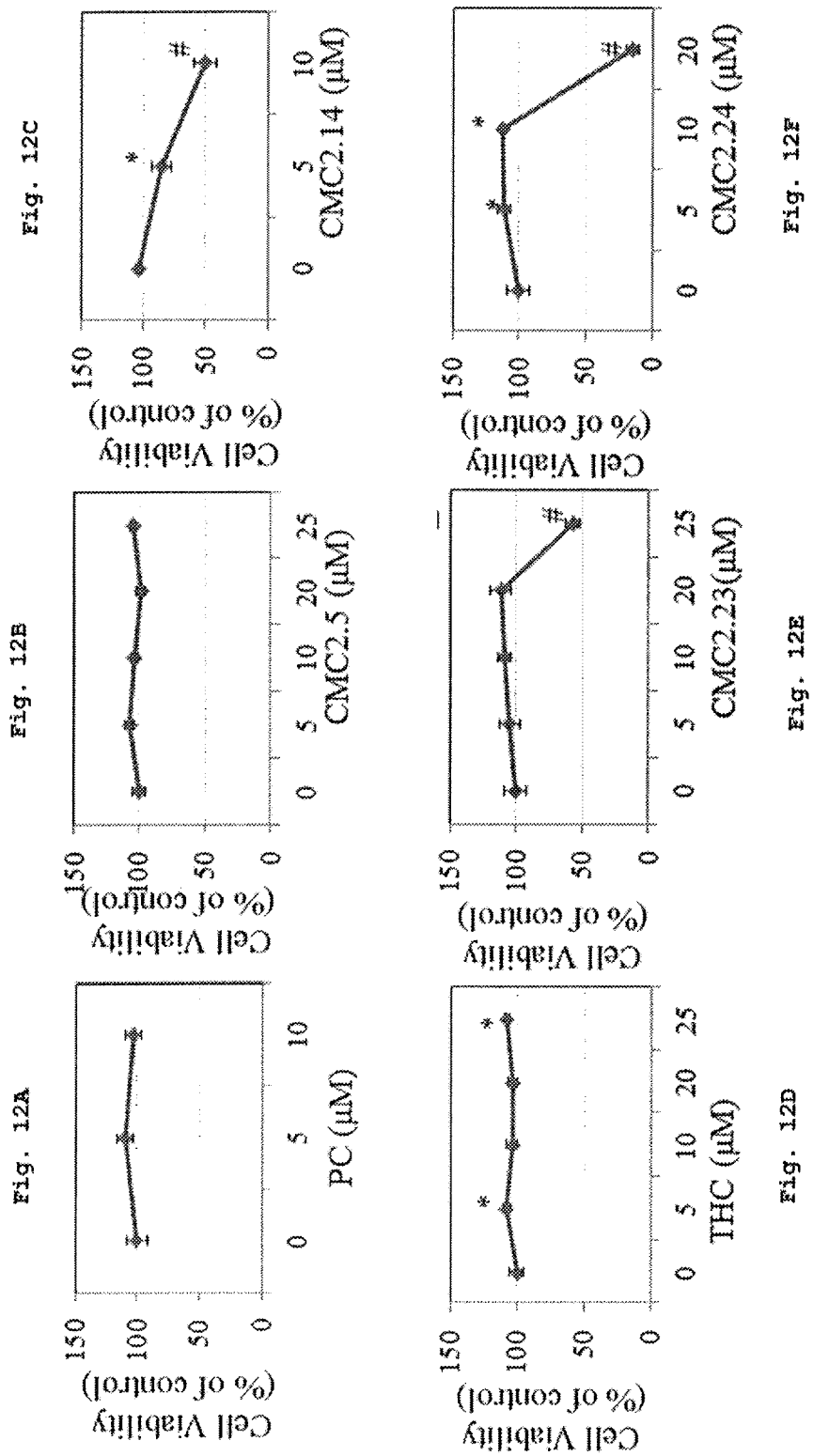

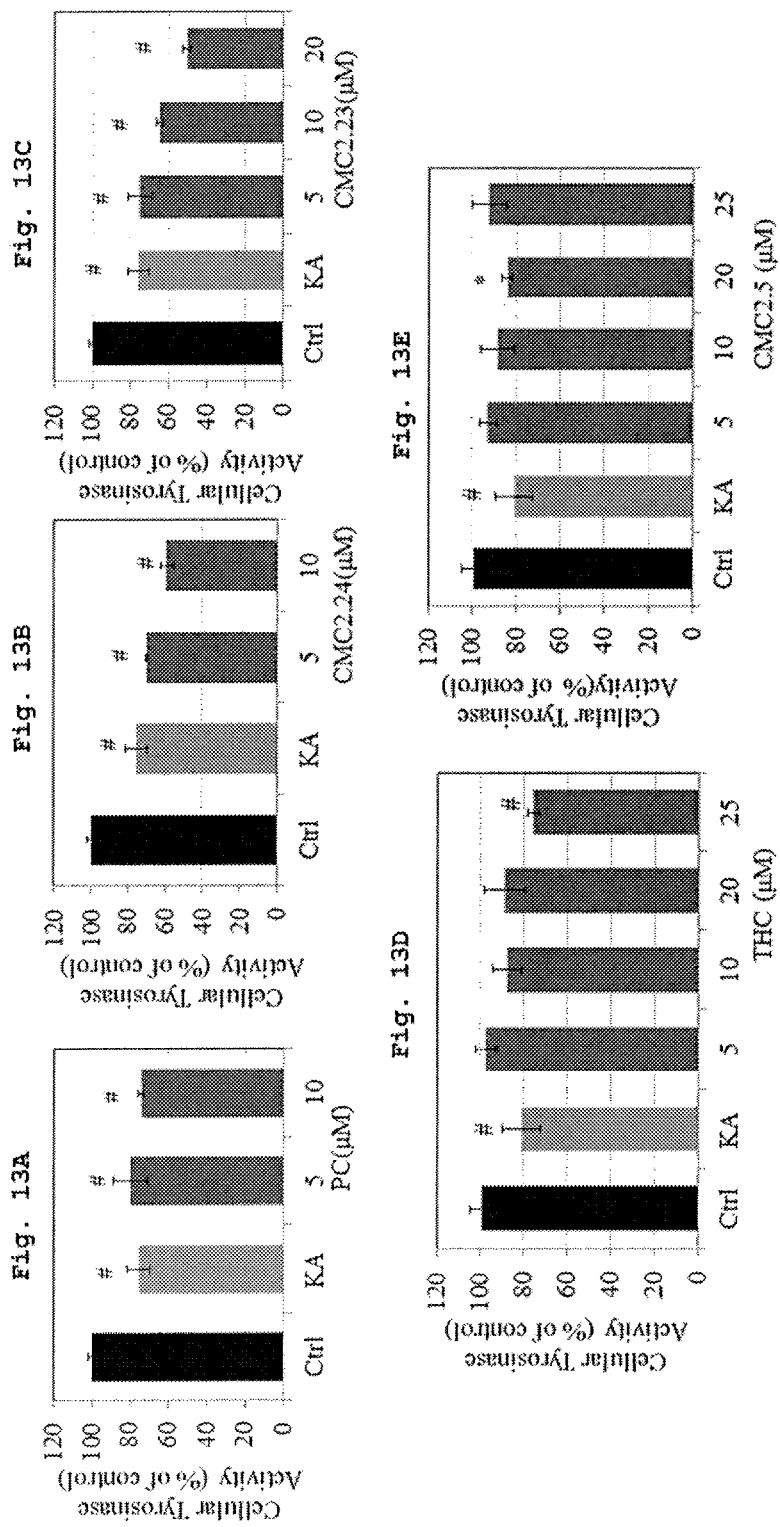

INHIBITION OF MELANOGENESIS BY CHEMICALLY MODIFIED CURCUMINS

This application claims priority of U.S. Provisional Application No. 62/393,429, filed Sep. 12, 2016, the contents of which are hereby incorporated by reference.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Curcumin is a naturally occurring compound of the curcuminoid family, isolated originally from the plant *Curcuma longa*. The rhizome of this plant, specifically, is used to create the spice known as turmeric, and is a major component of the daily diet in many Asian countries. Even before the modern characterization of curcumin's molecular structure and functionality, it has long been used in traditional eastern medicines.

With its natural medicinal history in mind, curcumin has been studied extensively over the past few decades in a wide variety of systems, and has been found to exhibit significant pleiotropic effects. These effects may be attributed to the chemistry of curcumin, consisting of two polyphenolic rings joined by a conjugated, flexible linker region with a β-diketone moiety at its center. The β-diketone moiety is capable of undergoing keto-enol tautomerization, though the enol form is more stable in both the solid phase and in solution (Gupta, S. C. et al. 2011) and is the dominant species at physiological pH (Gupta, S. C. et al. 2011; Zhang, Y. et al. 2012). The biological activities of curcumin are wide ranging: beyond having intrinsic antioxidant properties, it has been found to bind a wide spectrum of cellular constituents in vitro and in vivo, including inflammatory molecules, protein kinases, carrier proteins, cell survival proteins, structural proteins, the prion protein, antioxidant response elements, metal ions, and more (Gupta, S. C. et al. 2011). In addition, curcumin shows virtually no toxicity in humans (Gupta, S. C. et al. 2011; Ammon, H. P. T. et al. 1991).

While curcumin has been shown to have multiple beneficial effects, its poor oral absorption and lack of solubility in physiological fluid has all but precluded its use as a medicinal substance. Therefore, novel chemically-modified curcumins with enhanced pharmacokinetic and pharmacodynamic properties are needed.

Melanocytes are specialized cells which originate from the neural crest and have a key role in synthesis of melanin, a biopolymeric pigment inside organelles called melanosomes which are secreted and transferred to keratinocytes in the epidermis. Melanosomes progress through four stages of maturation [Cichorek, M. et al. 2013]. Melanocytes are present in basal layer of the epidermis and connect to neighboring keratinocytes via dendrites and one melanocyte contacts up to 30-40 keratinocytes to transfer melanin [Fitzpatrick, T. B. et al. 1963]. The process involves synthesis, packaging, transfer and uptake of melanin by keratinocytes [Ando, H. et al. 2012] which is ultimately responsible for skin coloration. Melanin provides UV photo-protection and scavenges free radicals; however, an excessive production of melanin in the skin can lead to hyperpigmentation, also called as hypermelanosis, and is associated with medical skin disorders such as melasma, post-inflammatory hyperpigmentation (PIH) and lentigosenilis (LS). It also causes significant psychosocial burden.

Tyrosinase (EC 1.14.18.1) is the rate-limiting enzyme in melanin synthesis pathway which catalyzes the conversion of L-tyrosine to L-Dopa and subsequent conversion to L-Dopaquinone. Tyrosinase is a membrane-bound glycoprotein consisting of two copper atoms in its active site [Chang, T. S. 2009]. Hence, compounds which can chelate copper can inhibit tyrosinase activity. The most popular commercial skin whitening agents, such as kojic acid, hydroquinone and arbutin (glycosylated hydroquinone) are tyrosinase inhibitors. However, all these exhibit serious side-effects; kojic acid causes pigmented contact dermatitis [García-Gavín, J. et al. 2010], hydroquinone is carcinogenic [Kooyers, T. et al. 2006] and arbutin has potent genotoxicity [Cheng, S. L. et al. 2007]. These limitations have prompted an interest in identifying novel and natural plant-derived compounds without adverse effects, for treatment of hyperpigmentation both in cosmetic and clinical settings.

SUMMARY OF THE INVENTION

The present invention provides a method of treating a subject afflicted with hyperpigmentation or of lightening the skin tone of a subject comprising administering to the subject an amount of a compound having the structure:

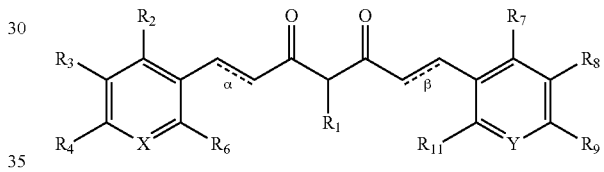

wherein bond α and β are each, independently, present or absent;

X is $CR_5$ or N; Y is $CR_{10}$ or N;

$R_1$ is $-SR_{12}$, $-SO_2R_{13}$, $-COR_{14}$, $-CSR_{14}$, $-C(=NR_{12})R_{14}$, $-C(=NH)R_{14}$, $-SOR_{12}$, $-POR_{12}$, $-P(=O)(OR_{12})(OR_{13})$, or $-P(OR_{12}).(OR_{13})$, wherein $R_{12}$ is $C_{1-10}$ alkyl, $C_{2-10}$ alkenyl, $C_{2-10}$ alkynyl, aryl, heteroaryl, or heterocyclyl;

$R_{13}$ is H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, or $-NR_{16}R_{17}$, wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted, or a salt or ester thereof, so as to thereby treat the subject or lighten the skin tone of the subject.

BRIEF DESCRIPTION OF THE FIGURES

FIG. 2A: Cell viability of B16F10 murine melanoma cells treated for 48 hours in the presence of different concentrations of PC, measured using MTS cytotoxicity assay. *-$p<0.05$ and #-$p<0.01$ vs. control FIG. 2B: Cell viability of B16F10 murine melanoma cells treated for 48 hours in the presence of different concentrations of CMC2.5, measured using MTS cytotoxicity assay. *-$p<0.05$ and #-$p<0.01$ vs. control FIG. 2C: Cell viability of B16F10 murine melanoma cells treated for 48 hours in the presence of different concentrations of CMC2.14, measured using MTS cytotoxicity assay. *-$p<0.05$ and #-$p<0.01$ vs. control FIG. 2D: Cell viability of B16F10 murine melanoma cells treated for 48 hours in the presence of different concentrations of THC, measured using MTS cytotoxicity assay. *-$p<0.05$ and #-$p<0.01$ vs. control FIG. 2E: Cell viability of B16F10 murine melanoma cells treated for 48 hours in the presence of different concentrations of CMC2.23, measured using MTS cytotoxicity assay. *-$p<0.05$ and #-$p<0.01$ vs. control FIG. 2F: Cell viability of B16F10 murine melanoma cells treated for 48 hours in the presence of different concentrations of CMC2.24, measured using MTS cytotoxicity assay. *-$p<0.05$ and #-$p<0.01$ vs. control

FIG. 3A: Mushroom tyrosinase activity quantification in cell-free system with different concentrations of PC, THC and CMCs measured using L-DOPA substrate. KA (500 µM) was used as positive control. *-$p<0.01$ and #-$p<0.001$ vs. control; letter a-$p<0.001$ vs. PC-20 µM; letter b-$p<0.001$ vs. PC-25 µM.

FIG. 3B: Copper chelating activity was measured in cell-free system using pyrocatechol violet (PV) dye method for PC, THC and CMCs. #-$p<0.001$ vs. control; letter a-$p<0.05$ vs. CMC2.24-25 µM. One-way ANOVA with Tukey's post-hoc test.

shows corresponding images at higher magnification for visualization of melanosomes of selected area shown by square. Black arrows indicate mature melanosomes (Stage III+IV) and white arrows indicate immature melanosomes (Stage I+II).

Figure 7:
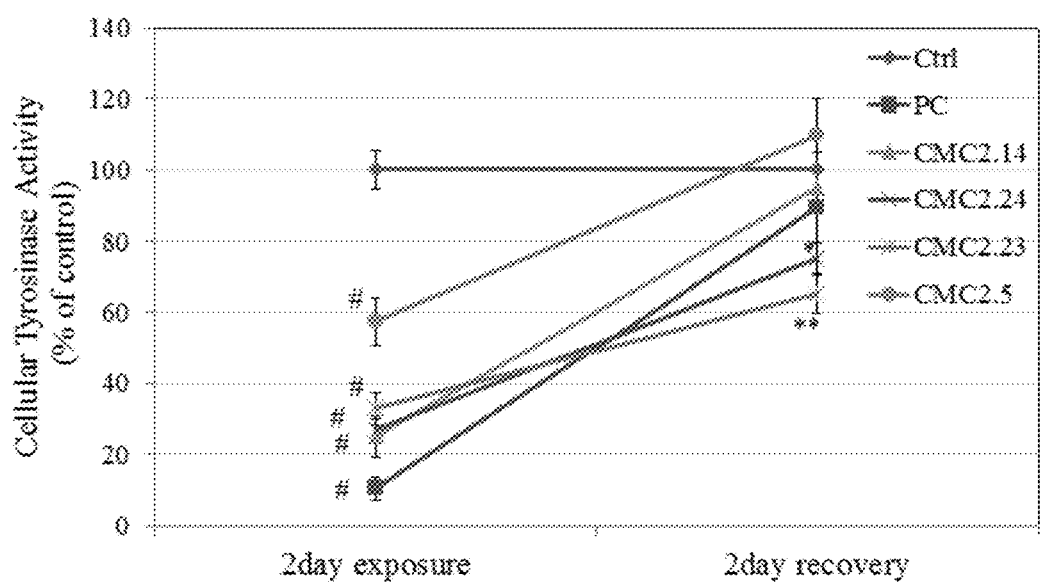

FIG. 7: Recovery study of intracellular tyrosinase activity in B16F10 cells—PC (10 µM), CMC2.14 (10 µM), CMC2.24 (20 µM), CMC2.5 (20 µM) and CMC2.23 (25 µM) #$p<0.01$ vs. control at 2 day exposure; #$p<0.01$ vs. control at 2 day exposure; *$p<0.05$ vs. control at 2 day recovery; **$p<0.01$ vs. control at 2 day recovery.

Figure 8:
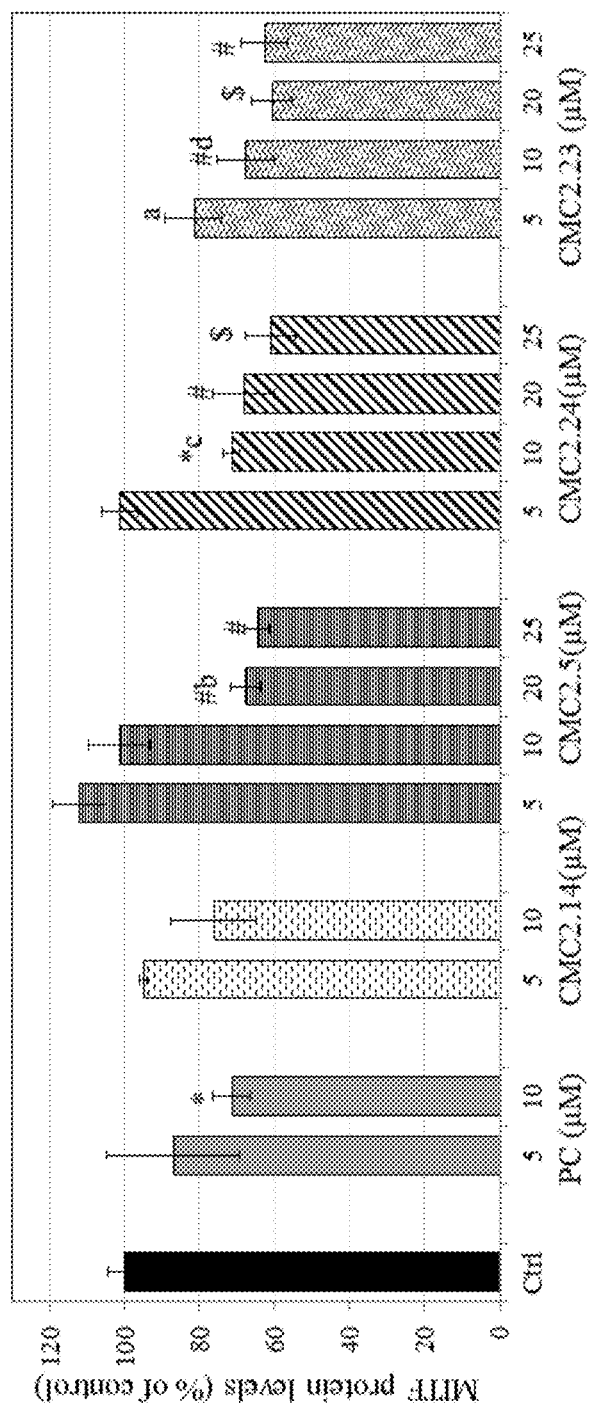

FIG. 8: MITF protein levels estimated by cell-based ELISA in cultures of B16F10 cells treated for 48 hours with different concentrations of PC and CMCs, *-$p<0.01$; #-$p<0.01$ and \$-$p<0.001$ vs. control; letter a-$p<0.05$ vs. CMC2.5-5 µM; letter b-$p<0.01$ vs. CMC2.5-10 µM; letter d-$p<0.01$ vs. CMC2.5-10 µM; letter c-$p<0.05$ vs. CMC2.24-5 µM; One-way ANOVA with Tukey's post-hoc test.

Figure 9A:
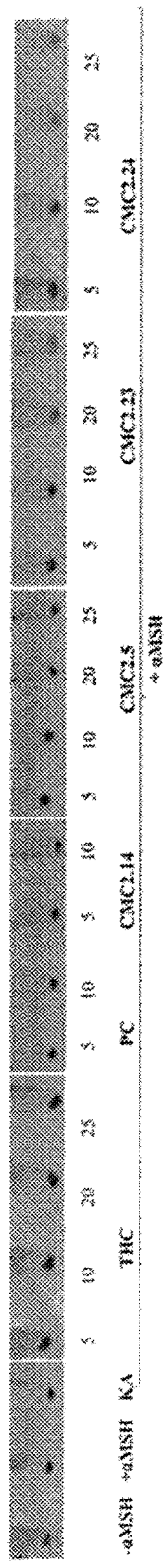

FIG. 9A: Effect of compounds on melanogenesis under αMSH-stimulated B16F10 cells. Melanin content estimation with different concentrations of PC, THC and CMCs showing panel of cell pellets with visible lightening.

Figure 9B:
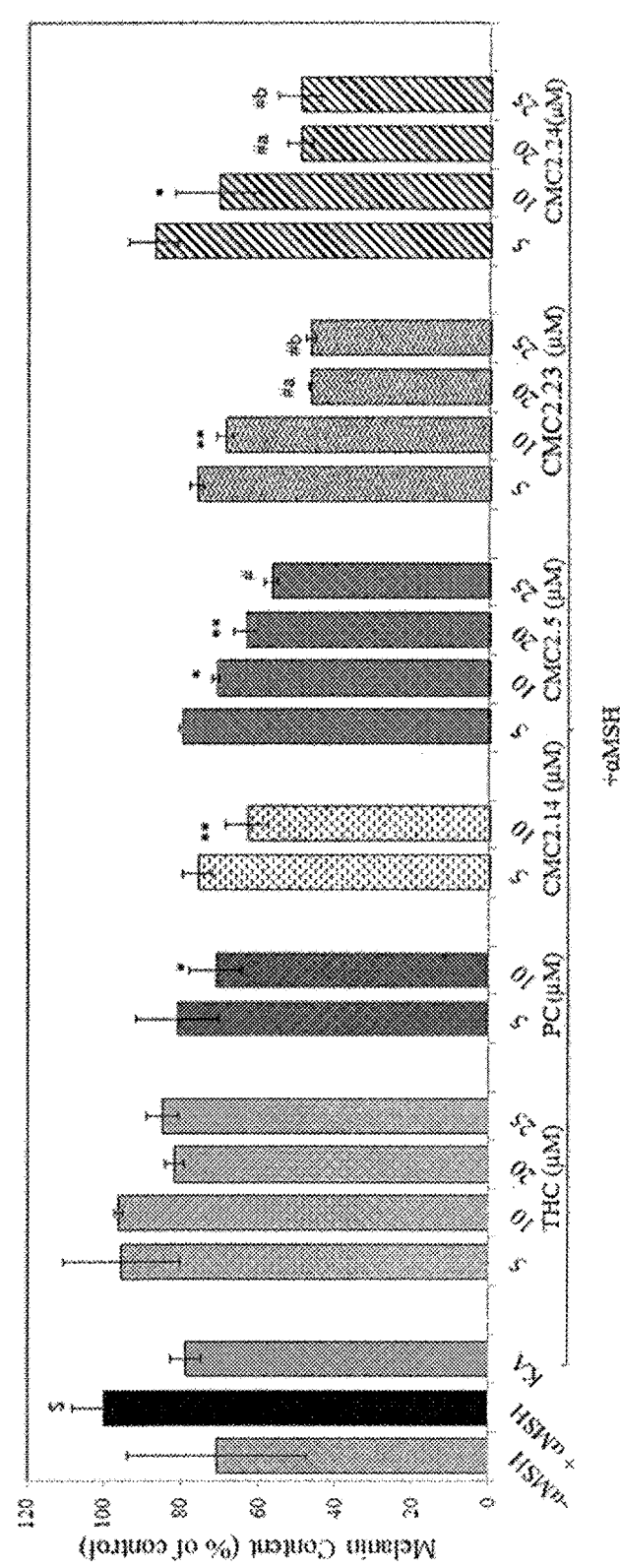

FIG. 9B: Quantification of melanin levels expressed as % of control in lysates. KA (500 µM) was used as positive control and control was treated with 0.1% DMSO. *-$p<0.01$ and #-$p<0.001$ vs. control; letter a-$p<0.05$ vs. THC at 5 µM; letter b-$p<0.01$ vs. THC at 10 µM. One-way ANOVA with Tukey's post-hoc test.

Figure 10A:
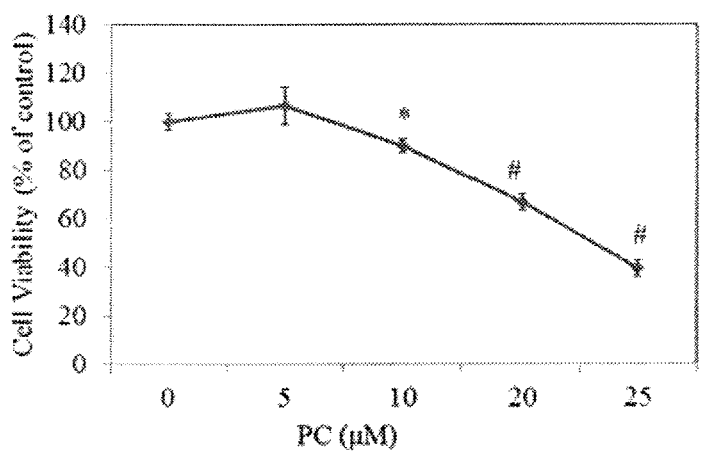

FIG. 10A: Cell viability of human keratinocytes (HaCaT) treated for 48 hours in the presence of different concentrations of PC, THC and CMCs. Controls were treated with 0.1% DMSO; A) PC, measured using MTS cytotoxicity assay. #-$p<0.01$ vs. control. One-way ANOVA with Dunnett's post-hoc test.

Figure 10B:
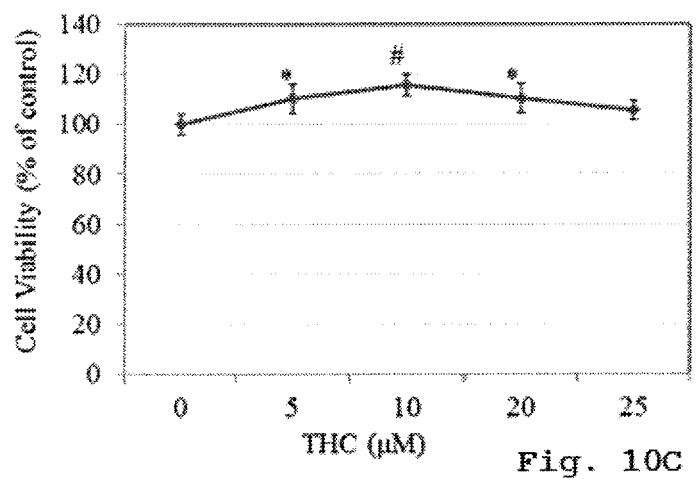

FIG. 10B: HaCaT treated with B) THC, measured using MTS cytotoxicity assay. #-$p<0.01$ vs. control. One-way ANOVA 644 with Dunnett's post-hoc test.

Figure 10C:
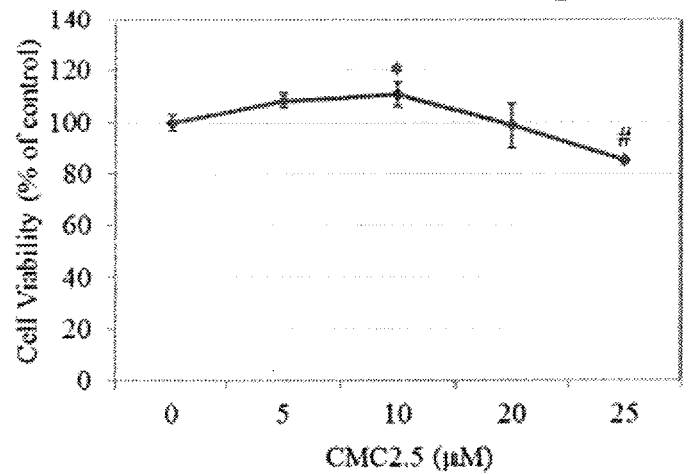

FIG. 10C: HaCaT treated with C) CMC2.5, measured using MTS cytotoxicity assay. #-$p<0.01$ vs. control. One-way ANOVA 644 with Dunnett's post-hoc test.

Figure 10D:
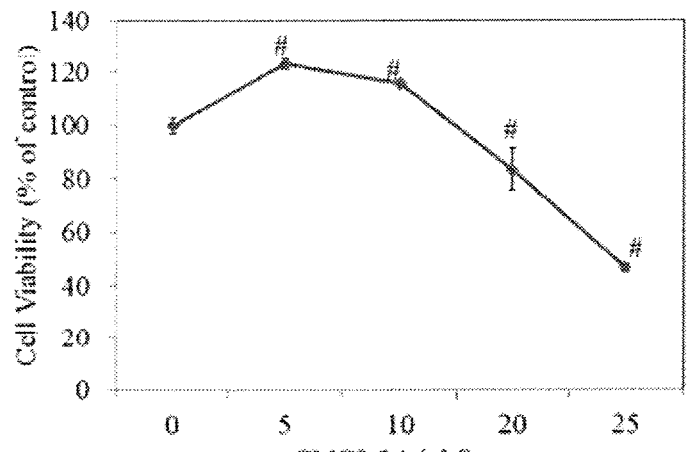

FIG. 10D: HaCaT treated with D) CMC2.14, measured using MTS cytotoxicity assay. #-$p<0.01$ vs. control. One-way ANOVA 644 with Dunnett's post-hoc test.

Figure 10E:
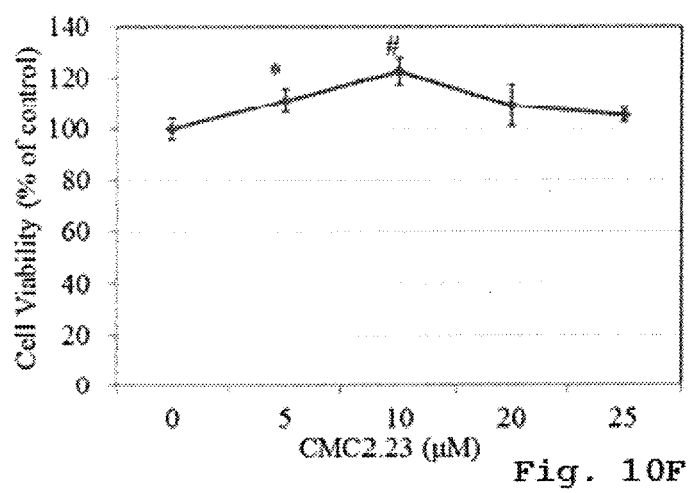

FIG. 10E: HaCaT treated with E) CMC2.23, measured using MTS cytotoxicity assay. #-$p<0.01$ vs. control. One-way ANOVA 644 with Dunnett's post-hoc test.

Figure 10F:
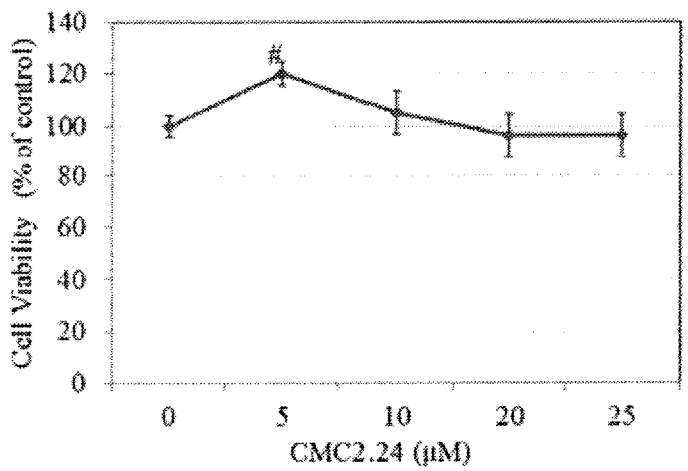

FIG. 10F: HaCaT treated with F) CMC2.24, measured using MTS cytotoxicity assay. #-$p<0.01$ vs. control. One-way ANOVA 644 with Dunnett's post-hoc test.

Figure 10G:
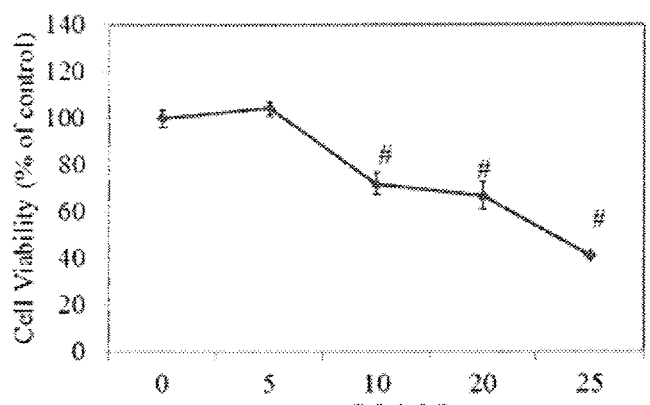

FIG. 10G: Cell viability of normal human dermal fibroblasts (NHDF) treated for 48 hours in the presence of different concentrations of PC, THC and CMCs. Controls were treated with 0.1% DMSO; A) PC, measured using MTS cytotoxicity assay. #-$p<0.01$ vs. control. One-way ANOVA with Dunnett's post-hoc test.

Figure 10H:
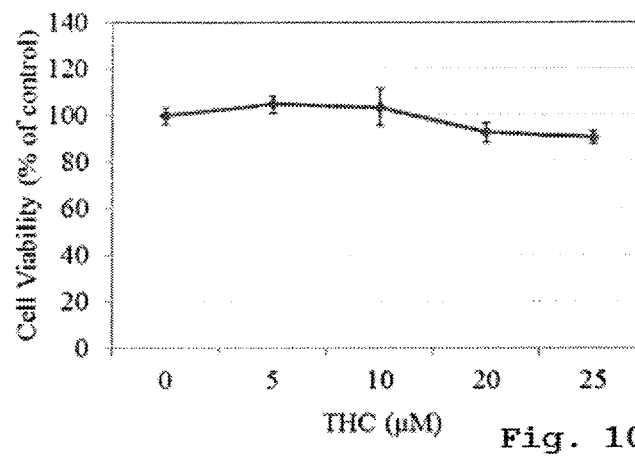

FIG. 10H: NHDF treated with H) THC, measured using MTS cytotoxicity assay. #-$p<0.01$ vs. control. One-way ANOVA 644 with Dunnett's post-hoc test.

Figure 10I:
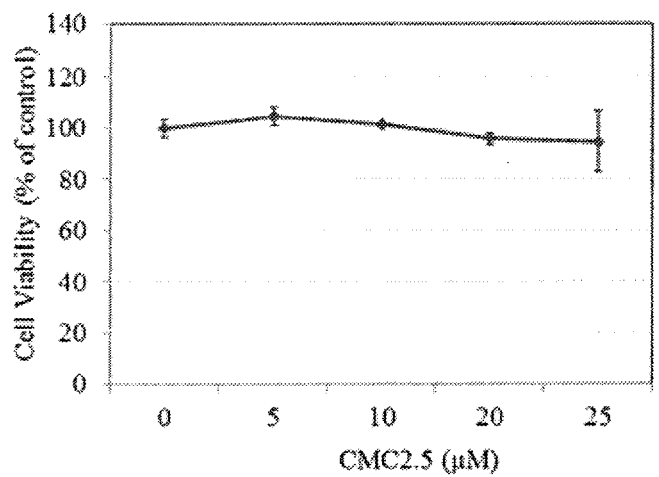

FIG. 10I: NHDF treated with I) CMC2.5, measured using MTS cytotoxicity assay. #-$p<0.01$ vs. control. One-way ANOVA 644 with Dunnett's post-hoc test.

Figure 10J:
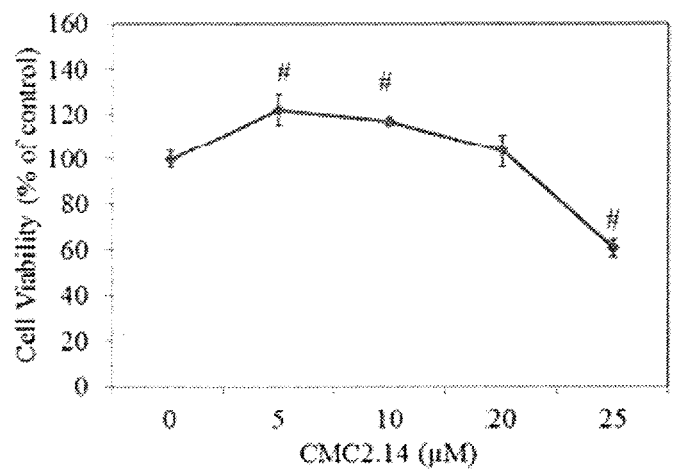

FIG. 10J: NHDF treated with J) CMC2.14, measured using MTS cytotoxicity assay. #-$p<0.01$ vs. control. One-way ANOVA 644 with Dunnett's post-hoc test.

Figure 10K:
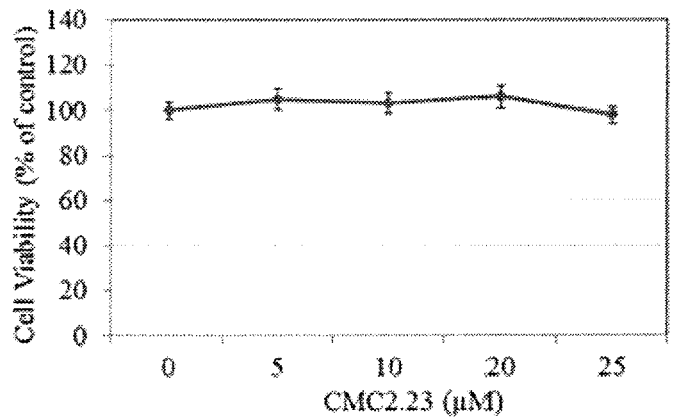

FIG. 10K: NHDF treated with K) CMC2.23, measured using MTS cytotoxicity assay. #-$p<0.01$ vs. control. One-way ANOVA 644 with Dunnett's post-hoc test.

Figure 10L:
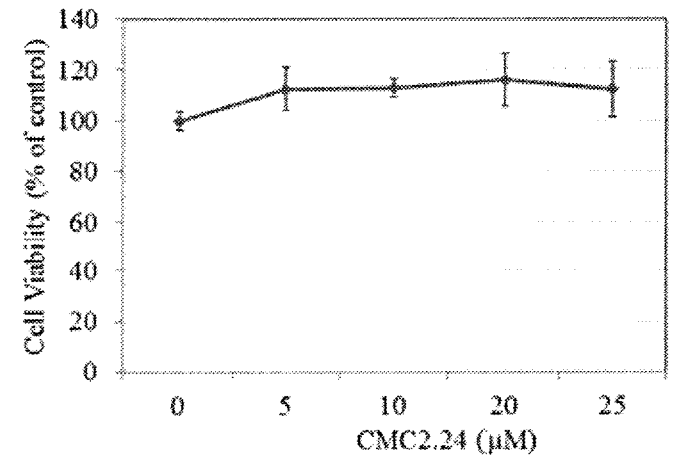

FIG. 10L: NHDF treated with L) CMC2.24, measured using MTS cytotoxicity assay. #-$p<0.01$ vs. control. One-way ANOVA 644 with Dunnett's post-hoc test.

Figure 11:
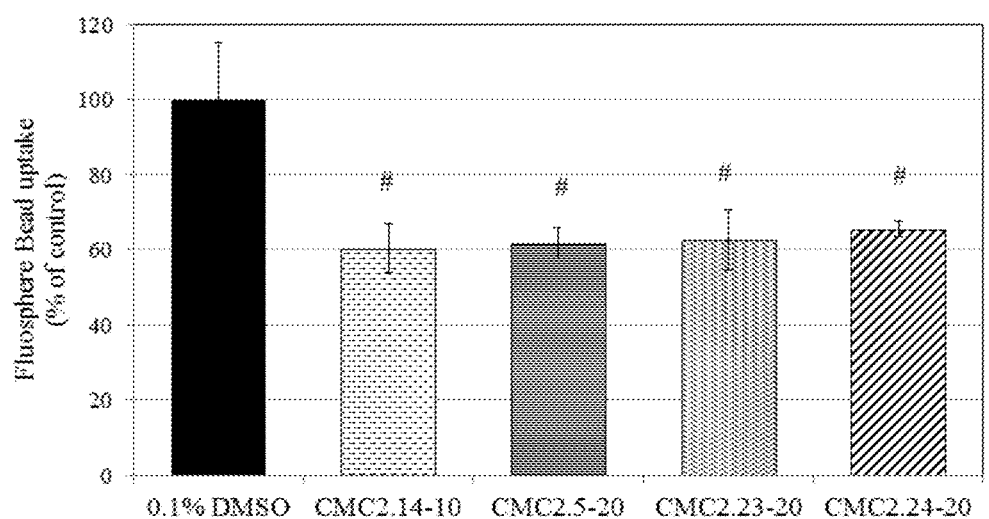

FIG. 11: Phagocytosis inhibition of Fluosphere beads in HaCaT cells after 24 hour exposure. 636 HaCaT cells were pretreated with CMC2.14 (10 µM), CMC2.5 (20 µM), CMC2.24 (20 µM) and 637 CMC2.23 (20 µM) for 48 hours and then Fluosphere beads were added for 24 hours. 638 Fluorescence of ingested beads was quantified on a fluorescence plate reader. #-$p<0.01$ vs. 639 control. One-way ANOVA with Dunnett's post-hoc test.

FIG. 12A: Human primary epidermal melanocyte— darkly pigmented (HEM-DP) viability in the presence of different concentrations of CMCs for 48 hrs. Measured by MTS assay treated with A) PC. *$p<0.05$; #$p<0.01$ vs. control. One-way ANOVA with Dunnetts test.

FIG. 12B: Treated with B) CMC2.5. *$p<0.05$; #$p<0.01$ vs. control. One-way ANOVA with Dunnetts test.

FIG. 12C: Treated with C) CMC2.14. *$p<0.05$; #$p<0.01$ vs. control. One-way ANOVA with Dunnetts test.

FIG. 12D: Treated with D) THC. *$p<0.05$; #$p<0.01$ vs. control. One-way ANOVA with Dunnetts test.

FIG. 12E: Treated with E) CMC2.23. *$p<0.05$; #$p<0.01$ vs. control. One-way ANOVA with Dunnetts test.

FIG. 12F. Treated with F) CMC2.24. *$p<0.05$; #$p<0.01$ vs. control. One-way ANOVA with Dunnetts test.

Figure 12H:
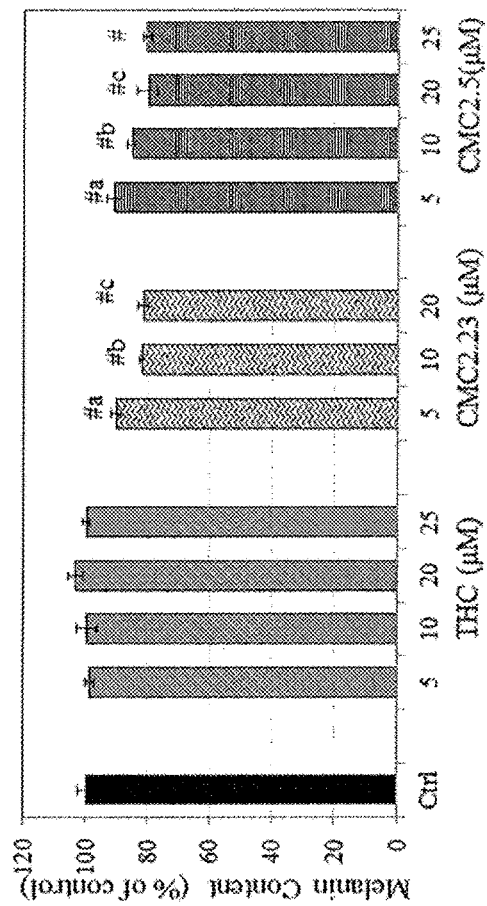
Figure 12G:
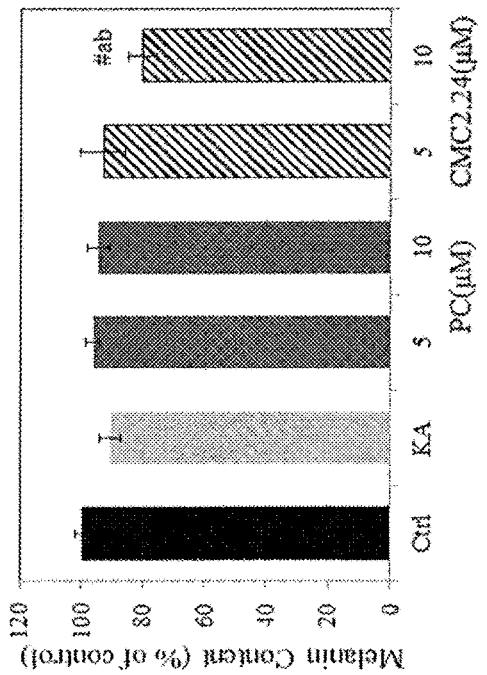

FIG. 12G. Melanin Content quantification in cultures of HEM-DP cells treated for 48 hours with different concentrations of CMCs. KA (1 mM) was used as positive control; G) PC and CMC2.24 and; B) THC and CMC2.23 and CMC2.5. *$p<0.05$; #$p<0.01$ vs. control. One-way ANOVA with Dunnetts test.

FIG. 12H. Melanin Content quantification in cultures of HEM-DP cells treated for 48 hours with different concentrations of CMCs. KA (1 mM) was used as positive control; H) THC and CMC2.23 and CMC2.5. *$p<0.05$; #$p<0.01$ vs. control. One-way ANOVA with Dunnetts test.

FIG. 13A: Cellular Tyrosinase activity study in HEM-DP cells treated for 48 hours with different concentrations of CMCs; KA (1 mM) was used as positive control; A) PC, B) CMC2.24, C) CMC2.23; D) THC and E) CMC2.5. *$p<0.05$; #$p<0.01$ vs. control. One-way ANOVA with Dunnetts test.

FIG. 13B: KA (1 mM) was used as positive control; B) CMC2.24. *$p<0.05$; #$p<0.01$ vs. control. One-way ANOVA with Dunnetts test.

FIG. 13C: KA (1 mM) was used as positive control; C) CMC2.23. *$p<0.05$; #$p<0.01$ vs. control. One-way ANOVA with Dunnetts test.

FIG. 13D: KA (1 mM) was used as positive control; D) THC. *$p<0.05$; #$p<0.01$ vs. control. One-way ANOVA with Dunnetts test.

FIG. 13E: KA (1 mM) was used as positive control; E) CMC2.5. *$p<0.05$; #$p<0.01$ vs. control. One-way ANOVA with Dunnetts test.

Figure 14:
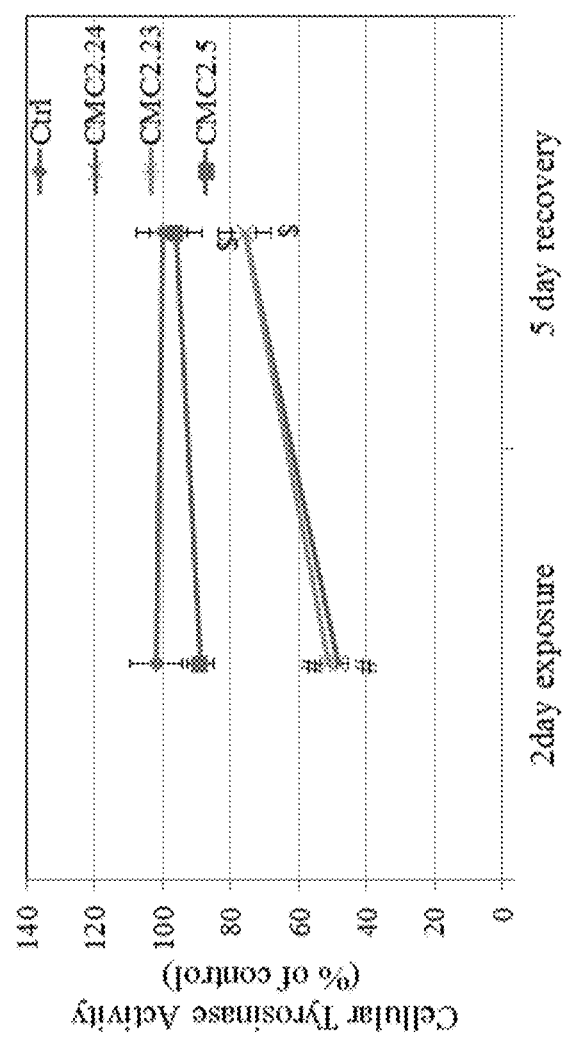

FIG. 14: Recovery of intracellular tyrosinase activity— CMC2.24 (10 M), CMC2.5 (20 M) and CMC2.23 (20 µM) #$p<0.01$ vs. control at 2 day exposure; \$$p<0.01$ vs. control at 5 day recovery.

DETAILED DESCRIPTION OF THE INVENTION

The present invention provides a method of treating a subject afflicted with hyperpigmentation comprising administering to the subject an amount of a compound having the structure:

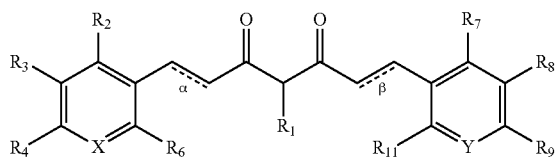

wherein bond α and β are each, independently, present or absent;

X is $CR_5$ or N; Y is $CR_{10}$ or N;

$R_1$ is $-SR_{12}$, $-SO_2R_{13}$, $-COR_{14}$, $-CSR_{14}$, $-C(=NR_{12})R_{14}$, $-C(=NH)R_{14}$, $-SOR_{12}$, $-POR_{12}$, $-P(=O)(OR_{12})(OR_{13})$, or $-P(OR_{12}).(OR_{13})$, wherein $R_{12}$ is $C_{1-10}$ alkyl, $C_{2-10}$ alkenyl, $C_{2-10}$ alkynyl, aryl, heteroaryl, or heterocyclyl;

$R_{13}$ is H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, or $-NR_{16}R_{17}$, wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}{}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted, or a salt or ester thereof, so as to thereby treat the subject.

In some embodiments, wherein the compound reduces melanin synthesis in the subject.

In some embodiments, wherein the compound inhibits melanogenesis in the subject.

In some embodiments, wherein the compound inhibits tyrosinase activity in the subject.

In some embodiments, wherein the compound lightens the skin tone of the subject relative to the subject's natural skin tone.

The present invention further provides a method of lightening the skin tone of a subject comprising administering to the subject an amount of a compound having the structure:

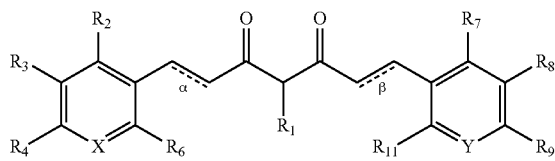

wherein bond α and β are each, independently, present or absent;

X is $CR_5$ or N; Y is $CR_{10}$ or N;

$R_1$ is $-SR_{12}$, $-SO_2R_{13}$, $-COR_{14}$, $-CSR_{14}$, $-C(=NR_{12})R_{14}$, $-C(=NH)R_{14}$, $-SOR_{12}$, $-POR_{12}$, $-P(=O)(OR_{12})(OR_{13})$, or $-P(OR_{12}).(OR_{13})$, wherein $R_{12}$ is $C_{1-10}$ alkyl, $C_{2-10}$ alkenyl, $C_{2-10}$ alkynyl, aryl, heteroaryl, or heterocyclyl;

$R_{13}$ is H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, or $-NR_{16}R_{17}$ wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}{}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted, or a salt or ester thereof, so as to thereby lighten the skin tone of the subject.

In some embodiments, wherein the compound reduces melanin synthesis in the subject.

In some embodiments, wherein the compound inhibits melanogenesis in the subject.

In some embodiments, wherein the compound inhibits tyrosinase activity in the subject.

In some embodiments, wherein the compound lightens the skin tone of the subject relative to the subject's natural skin tone.

The present invention yet further provides a method of inhibiting melanogenesis for reducing skin melanin levels in a subject comprising administering to the subject an amount of a compound having the structure:

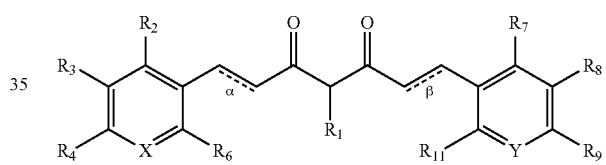

wherein bond α and β are each, independently, present or absent;

X is $CR_1$ or N; Y is $CR_{10}$ or N;

$R_1$ is $-SR_{12}$, $-SO_2R_{13}$, $-COR_{14}$, $-CSR_{14}$, $-C(=NR_{12})R_{14}$, $-C(=NH)R_{14}$, $-SOR_{12}$, $-POR_{12}$, $-P(=O)(OR_{12})(OR_{13})$, or $-P(OR_{12}).(OR_{13})$, wherein $R_{11}$ is $C_{1-10}$ alkyl, $C_{2-10}$ alkenyl, $C_{2-10}$ alkynyl, aryl, heteroaryl, or heterocyclyl;

$R_{13}$ is H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, or $-NR_{16}R_{17}$ wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}{}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted, or a salt or ester thereof, so as to thereby inhibit melanogenesis for reducing skin melanin levels in the subject.

In some embodiments, wherein in the compound α and β are each present.

In some embodiments, wherein in the compound α and β are each absent.

In some embodiments, wherein the compound has the structure:

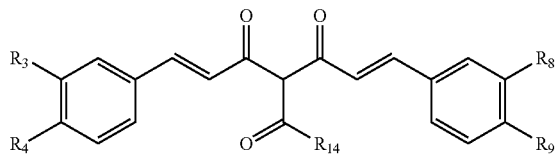

$R_3$, $R_4$, $R_8$ and $R_9$, are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and $R_{14}$ is methoxy, —$OR_{15}$, or —$NR_{16}R_{17}$, wherein $R_{15}$ is H, $C_{3-10}$ alkyl, $C_{2-10}$ alkenyl, $C_{2-10}$ alkynyl; and $R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

wherein each occurrence of alkyl, alkenyl, or alkynyl is branched or unbranched, unsubstituted or substituted, or a salt or ester thereof.

In some embodiments, wherein the compound has the structure:

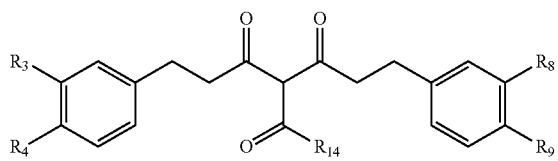

$R_3$, $R_4$, $R_8$ and $R_9$ are each independently, H, halogen, —$NO_2$, —CN, —$NR_{28}R_{29}$, —$NHR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and $R_{14}$ is methoxy, —$OR_{15}$, or —$NR_{16}R_{17}$, wherein $R_{15}$ is H, $C_{3-10}$ alkyl, $C_{2-10}$ alkenyl, $C_{2-10}$ alkynyl; and $R_{16}$ and $R_{17}$, are each, independently, H, $C_{1-10}$ alkyl, $C_{2-13}$ alkenyl, $C_{2-10}$ alkynyl, aryl, heteroaryl, or heterocyclyl;

wherein each occurrence of alkyl, alkenyl, or alkynyl is branched or unbranched, unsubstituted or substituted, or a salt or ester thereof.

In some embodiments, wherein $R_{14}$ is methoxy or —$NR_{16}R_{17}$, wherein $R_{16}$ and $R_{17}$ are each, independently, aryl or heteroaryl.

In some embodiments, wherein $R_3$, $R_4$, $R_8$ and $R_9$ are each independently, H or —$OR_{28}$, wherein $R_{28}$ is H or $C_{1-10}$ alkyl.

In some embodiments, wherein $R_3$, $R_4$, $R_8$ and $R_9$ are each —$OR_{28}$, wherein each $R_{28}$ is, independently, H or $C_{1-10}$ alkyl.

In some embodiments, wherein $R_3$, $R_4$, $R_8$, and $R_9$ are each, independently, H, —$OCH_3$, or —OH; and $R_{14}$ is methoxy or —$N(CH_3)_2$.

In some embodiments, wherein the compound has the structure:

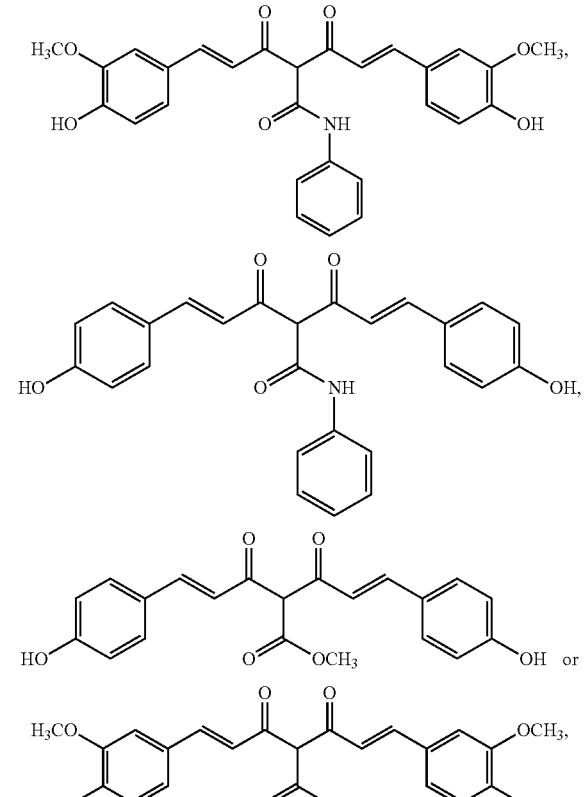

or a salt thereof.

In some embodiments, wherein the compound has the structure:

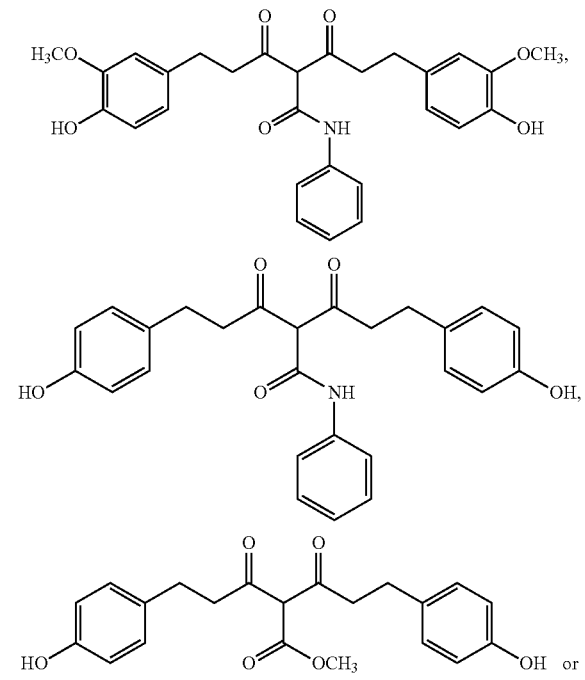

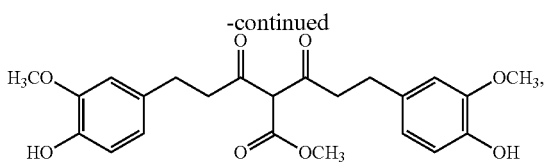

or a salt thereof.

In some embodiments, wherein the compound contains an amide group. In some embodiments, wherein the compound contains an ester group.

In some embodiments, wherein the compound is administered topically to the subject.

In some embodiments, the subject is afflicted with a skin pigmentation disorder.

In some embodiments, a method of decreasing production of melanin in a subject in need thereof comprising administering to the subject an amount of the compound of the present invention or a salt or ester thereof, so as to thereby decrease production of the melanin in the subject.

In some embodiments, a method of inhibiting melanogensis in a subject in need thereof comprising administering to the subject an amount of the compound of the present invention or a salt or ester thereof, so as to thereby inhibit melanogensis in the subject.

In some embodiments, the melanin is extracellular melanin.

In some embodiments, the melanin is intracellular melanin.

In some embodiments, the method inhibits keratinocyte uptake of extracellular melanin.

In some embodiments, the method reduces synthesis of extracellular melanin and intracellular melanin.

The present invention also provides a method of treating a subject afflicted with hyperpigmentation or of lightening the skin tone of a subject comprising administering to the subject an amount of a compound having the structure:

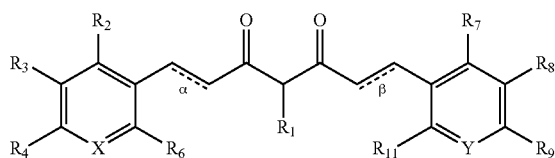

wherein bond α and β are each, independently, present or absent;

X is $CR_5$ or N; Y is $CR_{10}$ or N;

$R_1$ is H, $CF_3$, halogen, —$NO_2$, —$OCF_3$, —$OR_{12}$, —NHCO$R_{12}$, —CONR$_{12}$R$_{13}$, —CSNR$_{12}$R$_{13}$, —C(=NH)NR$_{12}$R$_{13}$, —SR$_{12}$, —SO$_2$R$_{13}$, —COR$_{14}$, —CSR$_{14}$, —C(=NR$_{12}$)R$_{14}$, —C(=NR$_{12}$) NR$_{13}$R$_{14}$, —SOR$_{12}$, —SONR$_{12}$R$_{13}$, —SO$_2$NR$_{12}$R$_{13}$, —P(O)R$_{12}$, —PH(=O)OR$_{12}$ —P(=O)(OR$_{12}$)(OR$_{13}$), or —P(OR$_{12}$)(OR$_{13}$), wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

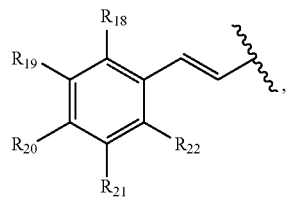

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, —$SOR_{23}$, —$POR_{23}$, —C(=S)R$_{23}$, —C(=NH)R$_{23}$, —C(=N)R$_{23}$, —P(=O)(OR$_{23}$)(OR$_{24}$), —P(OR$_{23}$)(OR$_{24}$), —C(=S)R$_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein when $R_1$ is H, then $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;

or a salt or ester thereof, so as to thereby treat the subject or lighten the skin tone of the subject.

In some embodiments, the method wherein the in the compound, $R_1$ is other than H.

In some embodiments, the method wherein the compound has the structure:

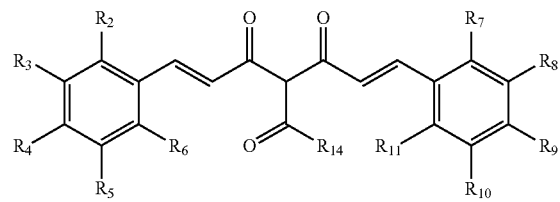

wherein $R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

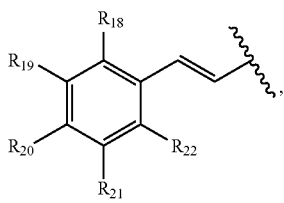

wherein $R_{15}$ is H, $C_{3-10}$ alkyl, $C_{2-10}$ alkenyl, $C_{2-10}$ alkynyl;
$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;
$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;
  wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;
$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;
  wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;
$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;
  wherein $R_{28}$ and $R_{29}$ are each, H, $CF_3$, $C_{1-10}$ alkyl, $C_{2-10}$ alkenyl, or $C_{2-10}$ alkynyl; and
wherein each occurrence of alkyl, alkenyl, or alkynyl is branched or unbranched, unsubstituted or substituted; and or a salt thereof.

In some embodiments, the method wherein the compound has the structure:

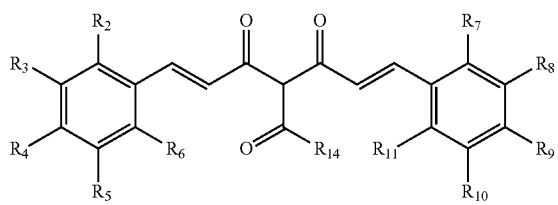

wherein $R_{14}$ is $C_{2-10}$ alkyl, $C_{2-10}$ alkenyl, $C_{2-10}$ alkynyl, heteroaryl, heterocyclyl, —$OR_{15}$, —$NR_{16}R_{17}$, or

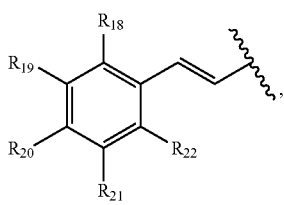

wherein $R_{15}$ is H, $C_{3-10}$ alkyl, $C_{2-10}$ alkenyl, $C_{2-10}$ alkynyl;
$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;
$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;
  wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;
$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;
  wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;
$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;
  wherein $R_{28}$ and $R_{29}$ are each, H, $CF_3$, $C_{1-10}$ alkyl, $C_{2-10}$ alkenyl, or $C_{2-10}$ alkynyl; and
wherein each occurrence of alkyl, alkenyl, or alkynyl is branched or unbranched, unsubstituted or substituted; and or a salt thereof.

In some embodiments, the method wherein the compound has the structure:

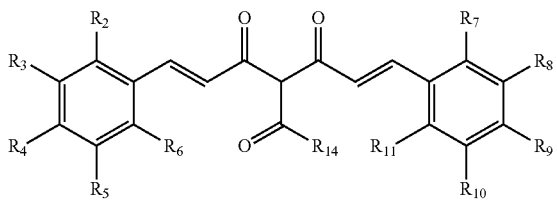

wherein $R_{14}$ is $C_{2-10}$ alkyl, $C_{2-10}$ alkenyl, $C_{2-10}$ alkynyl, heteroaryl, heterocyclyl, —$OR_{15}$, —$NR_{16}R_{17}$, or

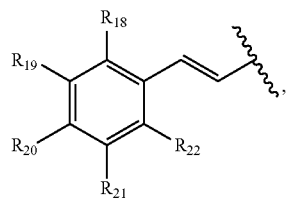

wherein $R_{15}$ is H, $C_{4-10}$ alkyl, $C_{2-10}$ alkenyl, $C_{2-10}$ alkynyl;
$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;
$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;
  wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;
$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;
  wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;
$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and or a salt thereof.

In some embodiments, the method wherein at least one of $R_2$, $R_3$, $R_4$, $R_5$, and $R_6$ and at least one of $R_7$, $R_8$, $R_9$, $R_{10}$, and $R_{11}$, are each, independently, —$OR_{28}$.

In some embodiments, the method wherein
$R_{14}$ is methoxy, —$OR_{15}$ or —$NR_{16}R_{17}$;
$R_{15}$ is H, $C_{3-10}$ alkyl, $C_{2-10}$ alkenyl, or $C_{2-10}$ alkynyl;
$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl; or a salt thereof.

In some embodiments, the method wherein
$R_{14}$ is methoxy or —$NR_{16}R_{17}$;
$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl; or a salt thereof.

In some embodiments, the method wherein
$R_{14}$ is —$OR_{15}$,
$R_{15}$ is H, $C_{3-10}$ alkyl, $C_{2-10}$ alkenyl, or $C_{2-10}$ alkynyl; or a salt thereof.

In some embodiments, the method wherein
$R_{14}$ is —$NR_{16}R_{17}$,
wherein $R_{16}$ and $R_{17}$ are each, independently, H or aryl;
$R_2$, $R_3$, $R_4$, $R_5$, $R_6$, $R_7$, $R_8$, $R_9$, $R_{10}$, and $R_{11}$ are each independently, H, —$NR_{28}R_{29}$, or —$OR_{28}$,
wherein $R_{28}$ and $R_{29}$ are each, H or $C_{1-10}$ alkyl; or a salt thereof.

In some embodiments, the method wherein
$R_{14}$ is —NH-phenyl;
$R_2$, $R_5$, $R_6$, $R_7$, $R_{10}$, and $R_{11}$ are each H;
$R_3$, $R_4$, $R_8$, and $R_9$ are each, independently, H, —OH, or —$OCH_3$;
or a salt thereof.

In some embodiments of the method, a compound having the structure:

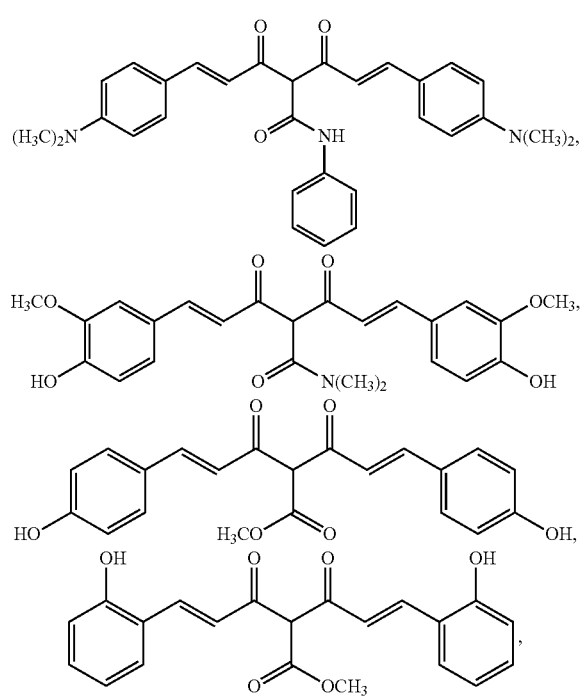

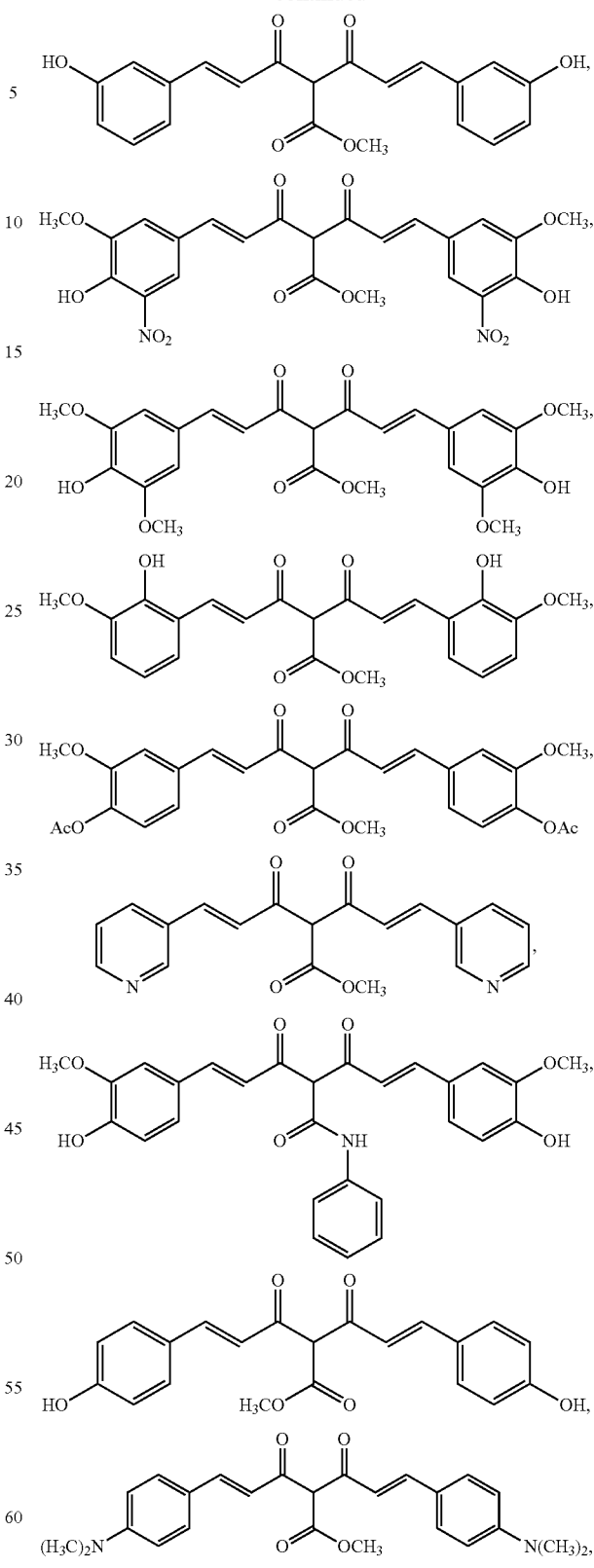

or a salt thereof.

In some embodiments of the method, a compound having the structure:

(2.23)
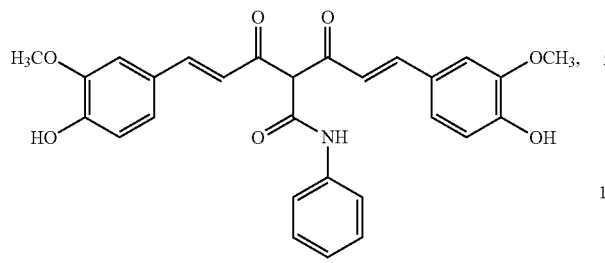

(2.24)
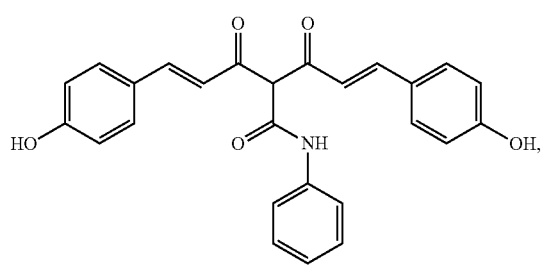

(2.14)
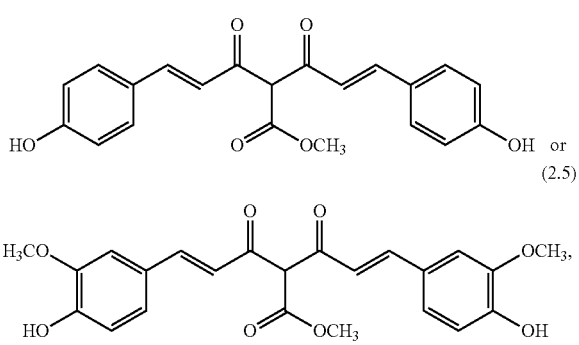

or a salt thereof.

In some embodiments of the method, a compound having the structure:

(2.231)
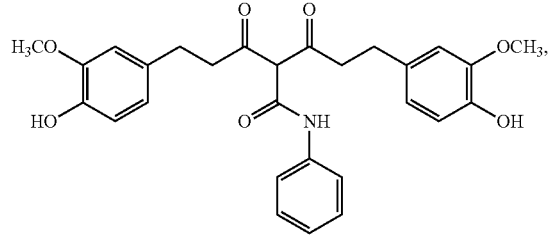

(2.241)
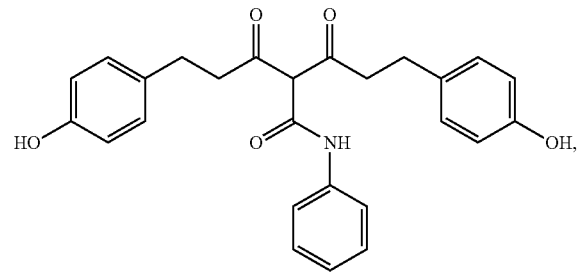

(2.141)

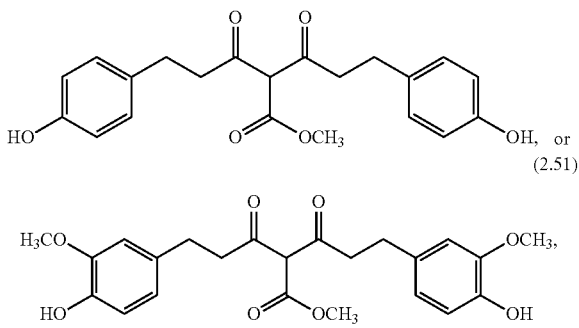

or (2.51)

or a salt thereof.

In some embodiments, melanin synthesis in the subject is reduced by at least 10%.

In some embodiments, melanin synthesis in the subject is reduced by at least 25%.

In some embodiments, melanin synthesis in the subject is reduced by at least 50%.

In some embodiments, melanin synthesis in the subject is reduced by 1 to 50%.

In some embodiments, melanin synthesis in the subject is reduced by 10 to 50%.

In some embodiments, melanin synthesis in the subject is reduced by 25 to 50%.

Melanogenesis herein relates to the production of melanin in melanocytes and/or transfer of melanin from melanocytes to keratinocytes.

The CMC's disclosed herein have improved solubility and greater metal binding capability and enhanced therapeutic anti-inflammatory effects and efficacy in vivo relative to curcumin or tetrahydrocurcumin.

In some embodiments, the compound is solubilized in a non-toxic organic solubilizing agent. A non-limiting example of a non-toxic organic solubilizing agent is N-methylglucamine, which is also known as "meglumine". In some embodiments, the compound is solubilized in dimethylsulfoxide. In some embodiments, the compound is solubilized in dimethylsulfoxide (less than 0.5% concentration).

This invention provides a pharmaceutical composition comprising a pharmaceutically acceptable carrier and of the above compounds.

Variations on the following general synthetic methods (Pabon, H. 1964) will be readily apparent to those skilled in the art and are used to prepare the compounds of the method of the present invention.

Scheme 1. Synthesis of curcumin analogues.

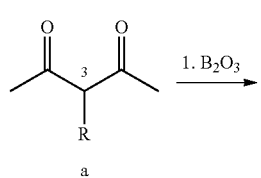

a

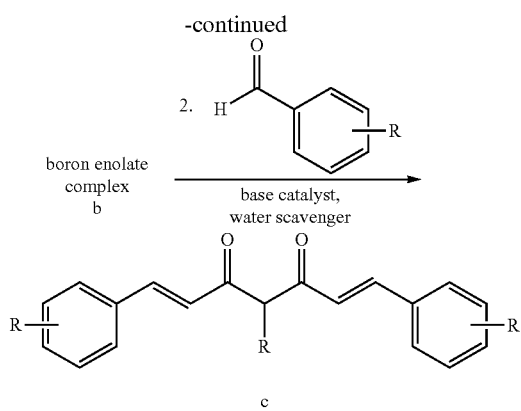

The synthesis of the curcumin analogues of the present invention can be carried out according to general Scheme 1. The R groups designate any number of generic substituents.

The starting material is provided by 2,4-pentanedione, which is substituted at the 3-carbon (see compound a). The desired substituted 2,4-pentanedione may be purchased from commercial sources or it may be synthesized using conventional functional group transformations well-known in the chemical arts, for example, those set forth in Organic Synthesis, Michael B. Smith, (McGraw-Hill) Second ed. (2001) and March's Advanced Organic Chemistry: Reactions, Mechanisms, and Structure, Michael B. Smith and Jerry March, (Wiley) Sixth ed. (2007), and specifically by Bingham and Tyman (45) and in the case of 3-aryl-aminocarbonyl compounds by Dieckman, Hoppe and Stein (46), the contents of which are hereby incorporated by reference. 2,4-pentanedione a is reacted with boron trioxide to form boron enolate complex b.

Boron enolate complex b is a complex formed by coordination of the enolate of compound a with boron. It is understood by those having ordinary skill in the art that the number of compound a enolates that may coordinate to boron as well as the coordination mode, i.e. monodentate versus bidentate, are variable so long as reaction, such as Knoevenagel condensation, at the C-3 carbon of the 2,4-pentanedione is suppressed.

Boron enolate complex b is then exposed to a benzaldehyde compound in the presence of a base catalyst and a water scavenger to form curcumin analogue c via aldol condensation. The ordinarily skilled artisan will appreciate that the benzaldehyde may possess various substituents on the phenyl ring so long as reactivity at the aldehyde position is not hindered. Substituted benzaldehyde compounds may be purchased from commercial sources or readily synthesized using aryl substitution chemistry that is well-known in the art. Suitable base catalysts for the aldol step include, but are not limited to, secondary amines, such as n-butylamine and n-butylamine acetate, and tertiary amines. Suitable water scavengers include, but are not limited to, alkyl borates, such as trimethyl borate, alkyl phosphates, and mixtures thereof. Other suitable reaction parameters have also been described by Krackov and Bellis in U.S. Pat. No. 5,679,864, the content of which is hereby incorporated by reference.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2$H and/or wherein the isotopic atom $^{13}$C. Accordingly, in the compounds provided herein hydrogen can be enriched in the deuterium isotope. It is to be understood that the invention encompasses all such isotopic forms.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, are intended to represent all isotopes of hydrogen, such as $^1$H, $^2$H, or $^3$H. Furthermore, any compounds containing $^2$H or $^3$H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n-1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH$_2$—(C$_5$H$_4$N), —CH$_2$—CH$_2$—(C$_5$H$_4$N) and the like.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

As used herein, the term "electron-withdrawing group" refers to a substituent or functional group that has the property of increasing electron density around itself relative to groups in its proximity. Electron withdrawing property is a combination of induction and resonance. Electron withdrawal by induction refers to electron cloud displacement towards the more electronegative of two atoms in a σ-bond. Therefore, the electron cloud between two atoms of differing electronegativity is not uniform and a permanent state of bond polarization occurs such that the more electronegative atom has a slight negative charge and the other atom has a slight positive charge. Electron withdrawal by resonance refers to the ability of substituents or functional groups to withdraw electron density on the basis of relevant resonance structures arising from p-orbital overlap. Suitable electron-withdrawing groups include, but are not limited to, —CN, —CF$_3$, halogen, —NO$_2$, —OCF$_3$, —OR$_{12}$, —NHCOR$_{12}$, —SR$_{12}$, —SO$_2$R$_{13}$, —COR$_{14}$, —CSR$_{14}$, —CNR$_{14}$, —C(=NR$_{12}$)R$_{14}$, —C(=NH)R$_{14}$, —SOR$_{12}$, —POR$_{12}$, —P(=O)(OR$_{12}$)(OR$_{13}$), or —P(OR$_{12}$)(OR$_{13}$), wherein R$_{12}$ and R$_{13}$ are each, independently, H, C$_{1-10}$ alkyl, C$_{2-10}$ alkenyl, C$_{2-10}$ alkynyl, aryl, heteroaryl, or heterocyclyl;

R$_{14}$ is C$_{2-10}$ alkyl, C$_{2-10}$ alkenyl, C$_{2-10}$ alkynyl, heteroaryl, heterocyclyl, methoxy, —OR$_{15}$, —NR$_{16}$R$_{17}$, or

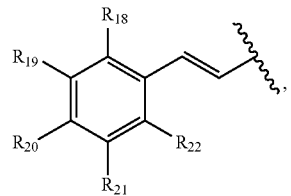

wherein R$_{15}$ is H, C$_{3-10}$ alkyl, C$_{2-10}$ alkenyl, C$_{2-10}$ alkynyl;

R$_{16}$ and R$_{17}$ are each, independently, H, C$_{1-10}$ alkyl, C$_{2-10}$ alkenyl, C$_{2-10}$ alkynyl, aryl, heteroaryl, or heterocyclyl;

R$_{18}$, R$_{19}$, R$_{21}$, and R$_{22}$ are each independently H, halogen, —NO$_2$, —CN, —NR$_{23}$R$_{24}$, —SR$_{23}$, —SO$_2$R$_{23}$, —CO$_2$R$_{23}$, —OR$_{25}$, CF$_3$, —SOR$_{23}$, —POR$_{23}$, —C(=S)R$_{23}$, —C(=NH)R$_{23}$, C(=NR$_{24}$)R$_{23}$, —C(=N)R$_{23}$, —P(=O)(OR$_{23}$)

($OR_{24}$), —$P(OR_{23})(OR_{24})$, —$C(=S)R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl.

In the subject invention, the biological activity of curcumin analogues is attributed in part to their ability to access and bind copper.

Without wishing to be bound by theory, it is believed that metal binding affinity arises from increased stability of the curcumin enolate formed by removal of hydrogen from the C-4 carbon, which then proceeds to form a complex with the metal. The stability of a carbanion, including an enolate, is directly related to the acidity of the ionizable hydrogen, such as an enolic hydrogen. In general, the stability of an enolate increases with increasing acidity of the enolic hydrogen. Herein, the enolic hydrogen refers to the hydrogen atom connected to the C-4 carbon of the curcumin skeleton.

The acidity of the enolic hydrogen of curcumin and its analogues can be enhanced by incorporation of an electron-withdrawing group at the C-4 carbon. Substituents which delocalize negative charge will enhance acidity and stability of the resulting carbanion, such as an enolate. Again, without wishing to be bound by theory, it is believed that the electron-withdrawing group allows the negative charge of the enolate to be delocalized into the electron-withdrawing group, thereby stabilizing the enolate, enhancing its stability, and increasing its metal binding affinity.

The choice of electron-withdrawing groups on the C-4 carbon and the choice of electron-donating groups on the aryl rings may be chosen using techniques well known by the ordinarily skilled artisan. In general, the electron donating ability of common substituents suitable for use on the aryl rings can be estimated by their Hammett σ values. The Hammett $\sigma_{para}$ value is a relative measurement comparing the electronic influence of the substituent in the para position of a phenyl ring to the electronic influence of a hydrogen substituted at the para position. Typically for aromatic substituents in general, a negative Hammett $\sigma_{para}$ value is indicative of a group or substituent having an electron-donating influence on a pi electron system (i.e., an electron-donating group) and a positive Hammett $\sigma_{para}$ value is indicative of a group or substituent having an electron-withdrawing influence on a pi electron system (i.e., an electron-withdrawing group). Similarly, Hammett $\sigma_{meta}$ value is a relative measurement comparing the electronic influence of the substituent in the meta position of a phenyl ring to the electronic influence of a hydrogen substituted at the meta position. A list of Hammett $\sigma_{para}$ and $\sigma_{meta}$ values for common substituents can be found in Lowry and Richardson, "Mechanism and Theory in Organic Chemistry", 3rd ed, p. 144. The effect of some substituents, including some electron-withdrawing groups, on C—H acidity can also be found on page 518 in Lowry and Richardson, "Mechanism and Theory in Organic Chemistry", 3rd ed, the content of which is hereby incorporated by reference.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutically acceptable salt.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles. Liposomes are also a pharmaceutically acceptable carrier as are slow-release vehicles, especially those intended for use in delivery of the active compounds to the epidermis.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect. A dosage unit of the compounds used in the method of the present invention may comprise a single compound or mixtures thereof with additional agents. The compounds can be introduced directly, e.g. by topical application, or other methods, onto a site of the skin condition, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for topical administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

In some embodiments, the topical application restricts delivery solely to the epidermis and/or avoids, or at least fails to facilitate, systemic delivery.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The compounds used in the method of the present invention may also be administered via transdermal routes, using those forms of transdermal skin patches well known to those of ordinary skill in that art. To be administered in the form of a transdermal delivery system, the dosage administration will generally be continuous rather than intermittent throughout the dosage regimen.

The compounds and compositions of the present invention can be introduced directly, e.g. by topical administration, to the afflicted area, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

As used herein, "treating" means preventing, slowing, halting, or reversing the progression of a disease or condition. Treating may also mean improving one or more symptoms of a disease or condition.

As used herein, "about" in the context of a numerical value or range means±10% of the numerical value or range recited or claimed, unless the context requires a more limited range.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

Chemically-modified curcumins may be relatively insoluble in water. Such compounds may be solubilized in a safe organic solubilizing agent, such as meglumine (ie., N-methyl glucamine which is a deoxy(methylamino) glucitol, a derivative of glucose) or dimethylsulfoxide (below 0.5%). Dimethylsulfoxide (below 0.5%) is generally recognized as safe for veterinary applications and have not been associated with toxicity to humans in topical applications.

The compounds of the present invention and derivatives thereof are described in and can be synthesized according to methods described in PCT International Publication Nos. WO 2010/132815 A9 and WO 2013/059203 A1, each of which are hereby incorporated by reference.

The National Institutes of Health (NIH) provides a table of Equivalent Surface Area Dosage Conversion Factors below (Table A) which provides conversion factors that account for surface area to weight ratios between species.

TABLE A

Equivalent Surface Area Dosage Conversion Factors

|      |        | To              |               |                 |              |              |
|------|--------|-----------------|---------------|-----------------|--------------|--------------|
|      |        | Mouse 20 g      | Rat 150 g     | Monkey 3 kg     | Dog 8 kg     | Man 60 kg    |
| From | Mouse  | 1               | ½             | ¼               | ⅙            | 1/12         |
|      | Rat    | 2               | 1             | ½               | ¼            | 1/7          |
|      | Monkey | 4               | 2             | 1               | ⅗            | ⅓            |
|      | Dog    | 6               | 4             | 1⅔              | 1            | ½            |
|      | Man    | 12              | 7             | 3               | 2            | 1            |

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Materials and Methods

Materials

MTS cytotoxicity assay (CellTiter Aqueous one) was purchased from Promega. Pure Curcumin (PC, 99% purity) was purchased from Selleck Chemicals. Tetrahydrocurcumin (THC, 96%, Sabiwhite™) was obtained via Biocogent LLC. The chemically synthesized curcumin derivatives—CMC2.24, CMC2.5, CMC2.14 and CMC2.23 (all 97% purity) were obtained from ChemMaster International through Dr. Francis Johnson. Pyrocatechol Violet (PV), copper sulfate, mushroom tyrosinase, L-DOPA, and kojic acid (KA) were purchased from Sigma. 2,2-diphenyl-1-picrylhydrazyl (DPPH) radical and 2',7'-dichlorodihydrofluorescein diacetate ($H_2DCFDA$) dye were purchased from Molecular Probes.

Cell Culture

B16F10 mouse melanoma cells (CRL-6475™) were obtained from ATCC (Manassas, Va.) and cultured in DMEM with 10% heat-inactivated fetal bovine serum (HI-FBS) and 1% antibiotics (penicillin-streptomycin). Human keratinocytes (HaCaT) cells were obtained from AddexBio (San Diego, Calif.) and primary human dermal fibroblasts (NHDF, purchased originally from Lonza) were obtained from Michael Ingrassia at Biocogent LLC (Stony Brook). Both these cells were cultured in DMEM with 10% HI-FBS and 1% antibiotics. Human primary epidermal melanocytes from darkly pigmented donor (HEM-DP) were obtained from Cascade Biologics. The cells were cultured using Medium 254 supplemented with 1% Human melanocyte growth supplement (HMGS, Cascade Biologics) and 1% antibiotics. Cells were detached using TrypLE Express (0.0.5%) and cultured in T-25 flasks.

MTS Cytotoxicity Assay

In order to test the four CMCs (CMC2.14, CMC2.24, CMC2.5 and CMC2.23) alongside PC and THC, for their effects on melanin content, we first screened their nontoxic concentrations using MTS cytotoxicity (Promega CellTiter Aqueous One) assay. MTS is a tetrazolium salt which is reduced to purple colored formazan upon reaction with mitochondrial dehydrogenases. Briefly, B16F10 cells were seeded at $4\times10^3$ cells/well in 96-well plates for 24 hrs. The test compounds were prepared from stocks (20 mM in DMSO) and further diluted using culture media (1:625 dilution) and added to the cells after 24 hrs, such that final DMSO concentrations in all groups were 0.16% which did not affect cell viability. Controls were treated with 0.16% DMSO. At the end of 48 hours, medium was aspirated and replaced by 100 µl of fresh media. MTS (20 µl) was added and incubated for 40 minutes and absorbance read at 490 nm using a Versamax® microplate reader. Cell viability was calculated from the absorbance values relative to control groups and expressed in %.

Melanin Content Quantification in B16F10 Cells

B16F10 cells were seeded at $1\times10^5$ cells/well in 1.5 ml media in 12-well plates and incubated for 24 hours. The media was then replaced with test compounds (PC, THC and 4 CMCs) at nontoxic doses (selected from MTS assay) and incubated for another 48 hours. For quantification of melanin content, cells were trypsinized and cell pellets were washed in PBS. Cell pellets were also visually observed for lightening of the intracellular pigment. After aspiration, 250 µL of 1N NaOH was added and heated to 70° C. to solubilize melanin. The aliquots were then transferred to a 96-well plate and absorbance was read at 475 nm using a microplate reader. A portion of the lysate was used to evaluate total protein content using BCA assay. The melanin absorbance was normalized by total protein content and expressed as % of control.

Mushroom Tyrosinase Activity

The direct effects of the compounds on tyrosinase enzyme activity were tested using mushroom tyrosinase enzyme with L-DOPA substrate. Briefly, 80 µl of all the 6 test compounds prepared at different concentrations in 50 mM sodium phosphate (pH 6.5) buffer was added to 96 wells followed by 100 µl of freshly prepared substrate solution (3 mM L-DOPA in buffer). The reaction was initiated by adding 20 µl of mushroom tyrosinase enzyme (final concentration of enzyme in wells was 3.5 µg/ml). The production of DOPAchrome was monitored by measuring the kinetics of absorbance increase at 475 nm (for 30 min every 30 seconds) at 30° C. using microplate reader (Versamax®). The slopes of the kinetic readings were calculated to determine and compare tyrosinase activity from control.

Copper Chelating Activity Assay

Metal ion chelation activity can be detected by pyrocatechol violet indicator assay which is similar to that reported in other studies with some modifications [Baek, S-H. et al. 2015]. Briefly, 100 µl of sample containing different concentrations of solutes were mixed with 50 mM sodium acetate buffer (pH 6.0) in a 96 well plate. Control group consisted of buffer only; KA at 500 µM was used as a positive control. Copper sulfate (2 mM; 10 µl) was added to the samples and incubated for 10 minutes. 10 µl of 2 mM pyrocatechol violet was then added and the plate was further incubated for 20 minutes. The absorbance was read at 632 nm using a microplate reader (Versamax). Lower absorbance compared to control was indicative of copper chelation.

Intracellular Tyrosinase Activity

We quantitated the cellular tyrosinase activity to delineate mechanism of melanogenesis inhibition by the compounds. Briefly, B16F10 cells were cultured in 24-well tissue culture plates at a density of $4\times10^4$ cells/well. After 24 hrs, media was changed and test compounds were added, and further incubated for 48 hrs. At the end of treatments, cells were trypsinized and cell pellets were washed in PBS and lysed with lysis buffer (containing 1% NP-40 to solubilize the normally membrane-bound enzyme and protease inhibitors) under ice for 20 minutes and then centrifuged to remove cellular debris. 50 µl of lysates were then aliquoted in 96-well microplate and 150 µl of 3 mM solution of freshly prepared L-DOPA in phosphate buffer, pH 6.8 was added.

The absorbance was then measured kinetically at 475 nm every 30 seconds for 40 minutes at 300° C. using microplate reader (Versamax®). The % inhibition of tyrosinase activity was calculated by determining melanin formation rates from measurements of the linear regions of the slopes of melanin content as a function of time and comparing computed rates of melanin formation in the presence of the test compounds to those of the controls.

DPPH Antioxidant Assay

Melanogenesis is often associated with higher oxidative stress and reactive oxygen species (ROS) generation. Hence, compounds which possess antioxidative activity can also act in inhibiting melanin production. DPPH is a stable free radical which changes color from purple to yellow upon reduction by antioxidant compounds by electron donation; the color change can be measured spectrophotometrically. PC, THC and CMCs were evaluated for antioxidant activity. Briefly, 2,2-Diphenyl-1-picrylhydrazyl (DPPH) was freshly prepared in methanol and mixed with different concentrations of the compounds in triplicates in a 96 well plate. The Negative Control group consisted of DPPH only and Ascorbic Acid (AA) at 100 µg/ml was used as a positive control. The final DPPH concentration was 100 µM and final volume was 200 ul in the plate (20 µl samples with 180 µl of DPPH). The plate was covered and incubated for 30 minutes. Absorbance was read at 517 nm. DPPH scavenging activity was reported as % relative to control.

Intracellular ROS Assay

Intracellular ROS generation was quantified using 2',7'-dichlorodihydrofluorescein diacetate ($H_2DCFDA$), a non-fluorescent dye which is trapped intracellularly by cleavage by intracellular esterases after reaction with reactive oxygen species (ROS); only the product, DCF, is fluorescent. For measuring intracellular ROS, B16F10 cells were seeded in 24 well plates at 4×104 cells/well. After 24 hours, media was aspirated and PC, THC and CMCs were added to the wells at different concentrations and further incubated for 48 hours. At the end of the incubations, the media was aspirated and cells were washed with PBS. DCFDA (Molecular Probes) was dissolved in DMSO to make 10 mM stock. DCFDA dye working stock (50 µM) was prepared by diluting the stock in DMEM (serum-free, phenol-red free and sodium pyruvate free) media and added to cells and further incubated for 45 minutes at 37° C. The cells were then washed with DPBS and fluorescence was read in bottom read mode, using a fluorescence microplate reader (Gemini EM Spectramax, Molecular Devices) set to excitation and emission wavelengths of 485 nm and 535 nm, respectively. Data was expressed as relative fluorescence % of treated vs. control.

Ultrastructural Study of Melanosome Maturation Stages Using TEM

In order to study the effects of CMCs on melanosome maturation, TEM was conducted to study ultrastructure and the effects were evaluated qualitatively. Briefly, B16F10 cells were seeded in six-well plates at 2×105 cells/well and treated with compounds (CMC2.5 at 20 µM, CMC2.14 at 10 µM, CMC2.23 at 25 µM and CMC2.24 at 20 µM) for 48 hours. The cells were detached as described herein, the pellets were washed in PBS and fixed in glutaraldehyde fixative overnight, and then processed for resin embedding. The images were observed using Tecnai BioTwin G TEM (FEI, OR, US), at 80 kV.

Recovery Study of Intracellular Tyrosinase Activity in B16F10 Cells

In order to establish reversibility of tyrosinase inhibition by the CMCs, we conducted a "recovery" study over a 2 day interval using the highest concentrations of the compounds which produced maximum tyrosinase activity inhibition without toxicity. B16F10 were plated in six-well plates at 3.5×104 cells/well and compounds were added (PC-10 µM, CMC2.14-10 µM, CMC2.5-20 µM, CMC2.23-25 µM and CMC2.24 at 20 µM) next day. Tyrosinase activity in one set of cultures after detachment and lysis as described herein was estimated after 2 day exposure while another set of cultures were continued with fresh media without the compounds to study reversibility of tyrosinase activity inhibition for another 2 days. Results are expressed as % tyrosinase activity for both 2 day exposure and 2 day recovery post 2 day exposure.

MITF Protein Levels Measurement in B16F10 Cells

MITF is the master regulator of melanogenesis and a known transcription factor for tyrosinase gene. The effects of PC and CMCs on micropthalmia transcription factor (MITF) proteins levels were assayed using a cell-based ELISA (LifeSpan Biosciences, Seattle). Briefly, B16F10 cells were cultured in a 96-well plate at 1×104 cells/well for 24 hours and then media was replaced with fresh media containing compounds in 0.1% DMSO for further 48 hours. The cells were then fixed and subsequent steps were conducted based on manufacturer instructions. The absorbance of MITF expression levels were normalized by absorbance of crystal violet stain (0.05%) and data was reported as % of control.

Melanin Content Measurement in αMSH-Stimulated B16F10 Cells.

UV irradiation is known to produce α-MSH, a pro-melanogenic stimulus and in order to test if CMCs exhibited antimelanogenic activity in presence of hormone stimulation; we tested the compounds in presence of MSH. B16F10 cells were seeded at 1×105 cells/well in 12-well plates and incubated for 24 hours. The test compounds were then added in presence or absence of αMSH (100 nM), and further incubated for another 48 hours. For evaluation of melanin content, cells were trypsinized, washed in PBS and then 250 µL of 1N NaOH was added and heated to 70° C. to solubilize melanin. The aliquots were then transferred to a 96-well plate and absorbance was read at 475 nm using microplate reader. The absorbance of melanin was normalized by total protein contents and reported as % of control.

MTS Cytotoxicity Test with Human Keratinocytes and Human Dermal Fibroblasts

For testing toxicity of PC, THC, and CMCs during 48 hours incubation with HaCaT cells, we conducted MTS cytotoxicity assay. Briefly, 2×104 cells/well were seeded in 96-well plates and after 24 hours, the compounds at concentrations of 5-25 µM were added to the wells and incubated for 48 hours. Absorbance was read after 1 hour of incubation of plates and results were expressed as % of control.

For testing cytotoxicity of the curcumin compounds exposed to normal human dermal fibroblasts, a protocol similar to that described immediately above was emploloyed. Briefly 5×103 cells/well were plated in 96 wells and compounds added for 48 hours. MTS assay was then conducted and plate incubated for 1 hour and then 100 µl of supernatants were aliquoted into 96 well plates and absorbance read at 490 nm using Versamax microplate reader.

Phagocytosis Assay Using Fluosphere Beads in Keratinocytes

The final steps of melanognesis in the skin involve transfer of melanin contained within matgure melanosomes from melanocytes to keratinocytes. In order to model melanosome uptake by keratinocytes in the presence of CMCs, we used uptake of fluosphere latex beads (0.5 µm, carboxylate-modified, Molecular Probes, Eugene, Oreg.) by a human keratinocyte cell line (HaCaT) as a model for melanosome uptake study; this model has been previously established [Cardinali G, et al. 2005; Cardinali, G. et al. 2008] to study phagocytosis by keratinocytes. HaCaT cells were cultured in 24 well plates (3.5×104 cells/well) for 48 hours and then media was replaced with fresh media containing CMCs (CMC2.14 at 10 µM, CMC2.5 at 20 µM, CMC2.23 at 20 µM and CMC2.24 at 20 µM). Control wells were treated with 0.1% DMSO. After 48 hours exposure, media was removed and wells were washed with PBS and Fluosphere bead solution was suspended in complete medium by sonication for 15 minutes was then diluted in complete medium before addition to the wells (180×107 beads/well) and further incubation for 24 hours. After the treatment, wells were washed in PBS and extracellular fluorescence was quenched using trypan blue (0.1% in PBS); Fluorescence intensity over the entire bottom surface of each well was measured at excitation/emission of 580/605 using the "well-scan" mode with average of 21 points/well for triplicate wells in a Gemini EM fluorescence plate reader. Controls without any beads were used as blank for background subtraction and results are reported as RFU values expressed as % relative to control.

MTS Cytotoxicity Test with Human Epidermal Melanocytes

For screening cytotoxicity of PC, THC and CMCs during 48 hours incubation on HEM-DP cells, we conducted MTS cytotoxicity assay. Briefly, 3×104 cells/well were seeded in 96 well plates and after 24 hours, compounds at various concentrations weres added to the wells and incubated for 48 hours. MTS reagent was added and incubated for 90 minutes and absorbance was read at 490 nm. The results are expressed as % relative to control.

Melanin Content Quantification in Human Epidermal Melanocytes

Melanin Content.

Primary cultures of human epidermal melanocytes from a darkly pigmented donor were seeded at 2.2×105 cells/well in 1.5 ml media in 12-well plates and incubated for 48 hours. The test compounds were added to cultures and controls were treated with 0.16% DMSO, and further incubated for another 48 hours. For evaluation of melanin content, cells in the wells were trypsinized and cell pellets were washed in PBS. After aspiration, 250 µL of 1N NaOH was added and heated to 70° C. to solubilize melanin. The aliquots were then transferred to a 96-well plate and absorbance was read at 475 nm using microplate reader. A portion of the lysate was used to evaluate total protein content using 239 bincinchonic acid (BCA) assay (Pierce BCA kit, Thermo Scientific). The absorbance of melanin was normalized to the total protein content for each lysate and reported as % of control.

Intracellular Tyrosinase Activity

We quantitated the cellular tyrosinase activity of human melanocytes based on established methods. Briefly, human epidermal melanocytes from a darkly pigmented donor (HEM-DP) were cultured in 12-well tissue culture plates at density of 1.5×105 cells/well. After 48 hrs. media was changed and test compounds were added, and further incubated for 48 hrs. At the end of treatments, cells were trypsinized and cell pellets were washed in PBS and lysed with lysis buffer under ice for 30 minutes and then centrifuged to remove cellular debris. 50 µl of lysates were then aliquoted in 96-well microplate and 150 µl of freshly prepared 3 mM L-DOPA was added. The absorbance was then measured kinetically at 475 nm every 30 seconds for 30 minutes at 30° C. using microplate reader (Versamax®). The % inhibition of tyrosinase activity was calculated by determining melanin formation rates from the linear range of the slopes of melanin formation over time for the different samples and calculating % inhibition from the measured velocities of melanin formation.

Recovery Study of Intracellular Tyrosinase Activity in Human Melanocytes

In order to study if the melanocytes could recover from inhibited tyrosinase activity after exposure to the CMCs, we employed a model for reversibility of inhibition of tyrosinase activity inhibition. This can establish safety of the compounds since irreversible inhibition of tyrosinase activity could damage melanocyte synthetic machinery with potential loss of the protective function of melanin. CMCs were used at highest concentration which gave potent inhibition of melanogenesis without toxicity (CMC2.24-10 µM, CMC2.23 at 20 µM and CMC2.5 at 20 µM). Briefly, HEM-DP were plated in 6-well plates at 2.3×105 cells/well and grown for 3 days and then CMCs were added. Tyrosinase activity was estimated after 2 day exposure in cellular lysates and another set of cultures were continued with fresh media without the compounds for further 5 days (with media change at day 3), in order to study reversibility of melanin inhibition.

Statistical Analysis

One-way analysis of variance (ANOVA) with Tukey's post-hoc test was run in experiments where all compounds were tested together while Dunnett's post-hoc test was used when compounds were compared individually vs. control. All the analyses were conducted using GraphPad Prism software (Version 4.0) and differences were considered statistically significant at p<0.05. All data are reported as Mean±SD.

Example 1. Effect of Compounds on Cytotoxicity in B16F10 Cells

Figure 1:
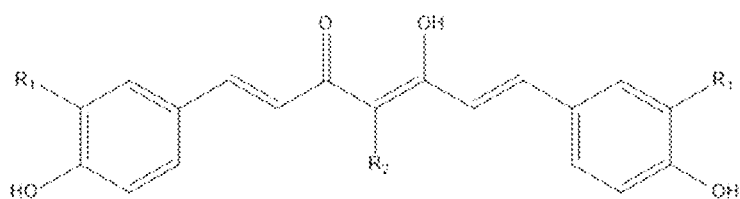
FIG. 1: Chemical structures of PC, THC and CMCs with parent skeleton.

MTS assay was conducted to screen the compounds (PC, THC and CMCs) for cytotoxicity and only select nontoxic ones to be further used for melanogenesis study. PC and CMC2.14 caused significant cytotoxicity at 20 and 25 µM. The mean value of cell viability was 24.44% and 16.55% for PC at 20 µM and 25 uM, respectively (FIG. 1A) while it was 73.31% and 53.6% for CMC2.14 (FIG. 1C). All the compounds with the exception of THC stimulated cell proliferation significantly at lower doses. For example, CMC 2.14 at 5 µM caused increase of 26.2% (p<0.01) and CMC2.24 caused increase of 40.7% (p<0.05) while PC at 5 µM also stimulated by 13% (p<0.05). CMC2.24 showed the maximal proliferative response out of the 4 derivatives. Overall, PC was found to be most cytotoxic. Based on the results, PC and CMC2.14 were used for further cellular studies at 5 and 10 µM only and THC, CMC2.14, CMC2.5, CMC2.24 and CMC2.23 were used in range 5-25 µM.

Example 2. Effect of Compounds on Melanin Synthesis in B16F10 Cells

Figure 2G:
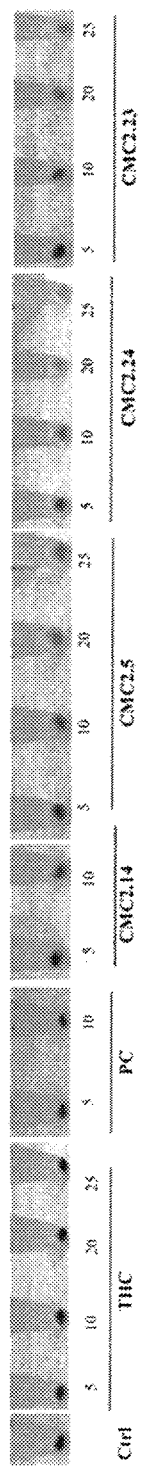
FIG. 2G: Melanin content estimation with different concentrations of PC, THC and CMCs showing panel of cell pellets with visible lightening.
Figure 2H:
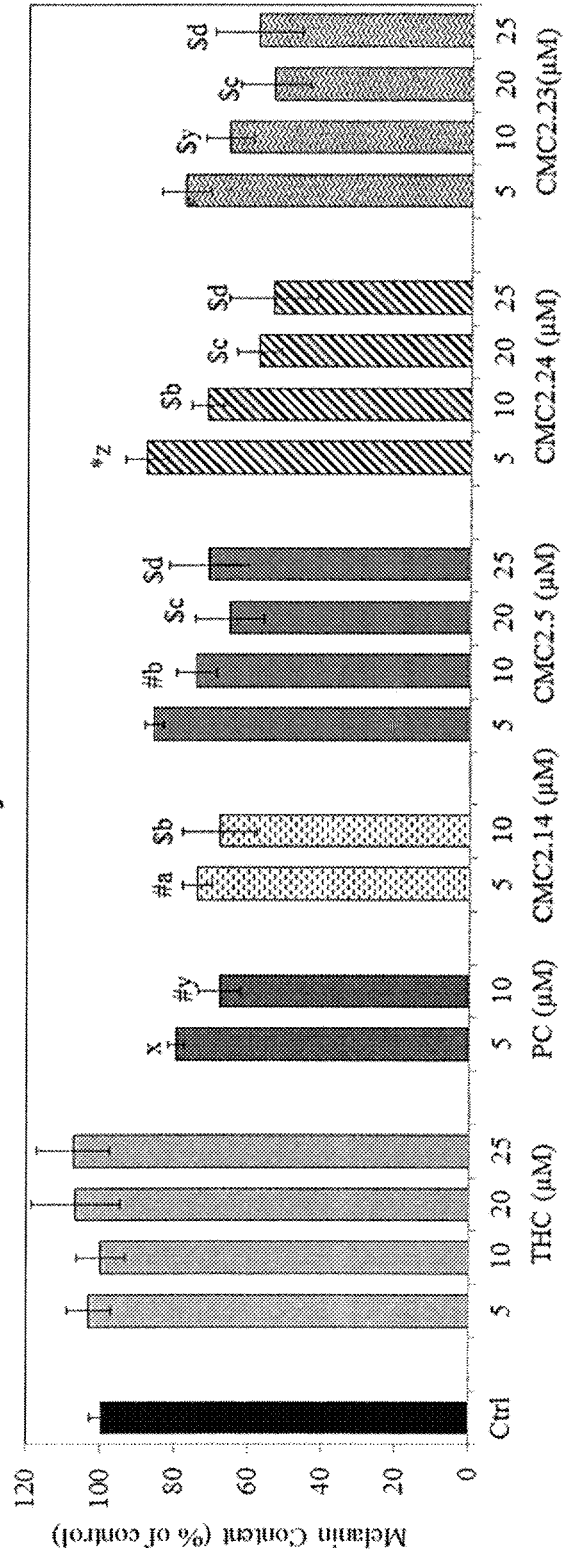
FIG. 2H: Quantification of melanin levels expressed as % of control in lysates. Control was treated with 0.1% DMSO and KA (500 µM) was used as positive control. *-$p<0.01$; #-$p<0.01$ and \$-$p<0.001$ vs. control; letter x-$p<0.05$ vs. THC-5 µM; letter y-$p<0.01$ vs. THC-10 µM; letter z-$p<0.01$ vs. THC-5 µM; letter a-$p<0.001$ vs. THC-5 µM; letter b-$p<0.001$ vs. THC-10 µM; letter c-$p<0.001$ vs. THC-20 µM; letter d-$p<0.001$ vs. THC-25 µM; One-way ANOVA with Tukey's post-hoc test. Results are average of two independent experiments conducted in duplicate. Cell pellet image panel shows representative images from one experiment.

Melanin content was estimated in cell pellets to study effects of compounds on inhibition of melanogenesis. FIG. 2H shows the results of the melanin contents of B16F10 cells treated with compounds (PC, THC, CMCs) for 48 hours. The panel (FIG. 2G) shows the cell pellets visibly lightening in case of CMC2.24 and CMC2.23 dose-dependently more than other groups and the melanin content estimation also showed that CMC2.24 and CMC2.23 showed the most potent inhibition. THC unexpectedly increased melanin content marginally (p>0.05) unlike PC which decreased it which indicates that the double bond conjugation in curcumin is critical for antimelanogenic activity; this activity is apparently lost upon removal of double bond conjugation to form THC. The levels of inhibition obtained by PC at 10 µM (32.14%) was similar to CMC2.5 at 20 µM (34.59%) and CMC2.14 at 10 µM (32.21%) (FIG. 2H, p<0.001). Higher inhibition of 46.4% was achieved by CMC2.24 at 20 µM and CMC2.23 at 25 µM. CMC2.23 also showed a similar profile. The other CMCs (2.23, 2.14 and 2.5) showed moderate inhibition which was similar across all the concentrations tested and there was no significant inhibition difference between the similar concentrations of the compounds. The CMCs also demonstrated similar inhibitory profile in case of αMSH stimulated B16F10 cells (FIG. 13) which confirms their utility for both spontaneous and homone-stimulated melanogenesis.

Example 3. Effect of Compounds on Mushroom Tyrosinase Activity in Cell-Free System As tyrosinase is the primary rate-limiting enzyme in melanogenesis pathway, we studied if the compounds inhibited melanin in part due to inhibition of tyrosinase. Mushroom tyrosinase activity was tested to screen the compounds to identify if the compounds had any direct inhibitory effect of the tyrosinase enzyme using L-DOPA as substrate. FIG. 3A shows the results of the tyrosinase activity treated with compounds (PC, THC, CMCs). Based on the results, CMC2.24 exhibited the greatest inhibitory activity with observed percentage inhibition of 35.4% at 20 and 38.2% at 25 µM which was significantly different from control and significant (p<0.001) as compared to PC. The other CMCs (2.23, 2.14 and 2.5) showed moderate inhibition which was similar across all the concentrations tested There was no significant difference between the observed extents of inhibition by similar concentrations of the compounds.

Example 4. Effect of Compounds on Copper Chelating Activity in Cell-Free System Since tyrosinase is a binuclear copper enzyme, we further studied if the compounds inhibited tyrosinase via copper chelation, for which the PV dye method was used and results are summarized in FIG. 3B. CMC2.24 at 20 µM showed significant (p<0.001) copper chelating activity of 11.86% compared to control, while all other CMCs and PC did not show any effect on copper chelating activity. Unexpectedly, THC significantly (p<0.001) chelated copper by 16.7% and 15.5% at 20 and 25 µM, respectively.

Figures 4A, 4B, 4C, 4D, 4E, 4F:
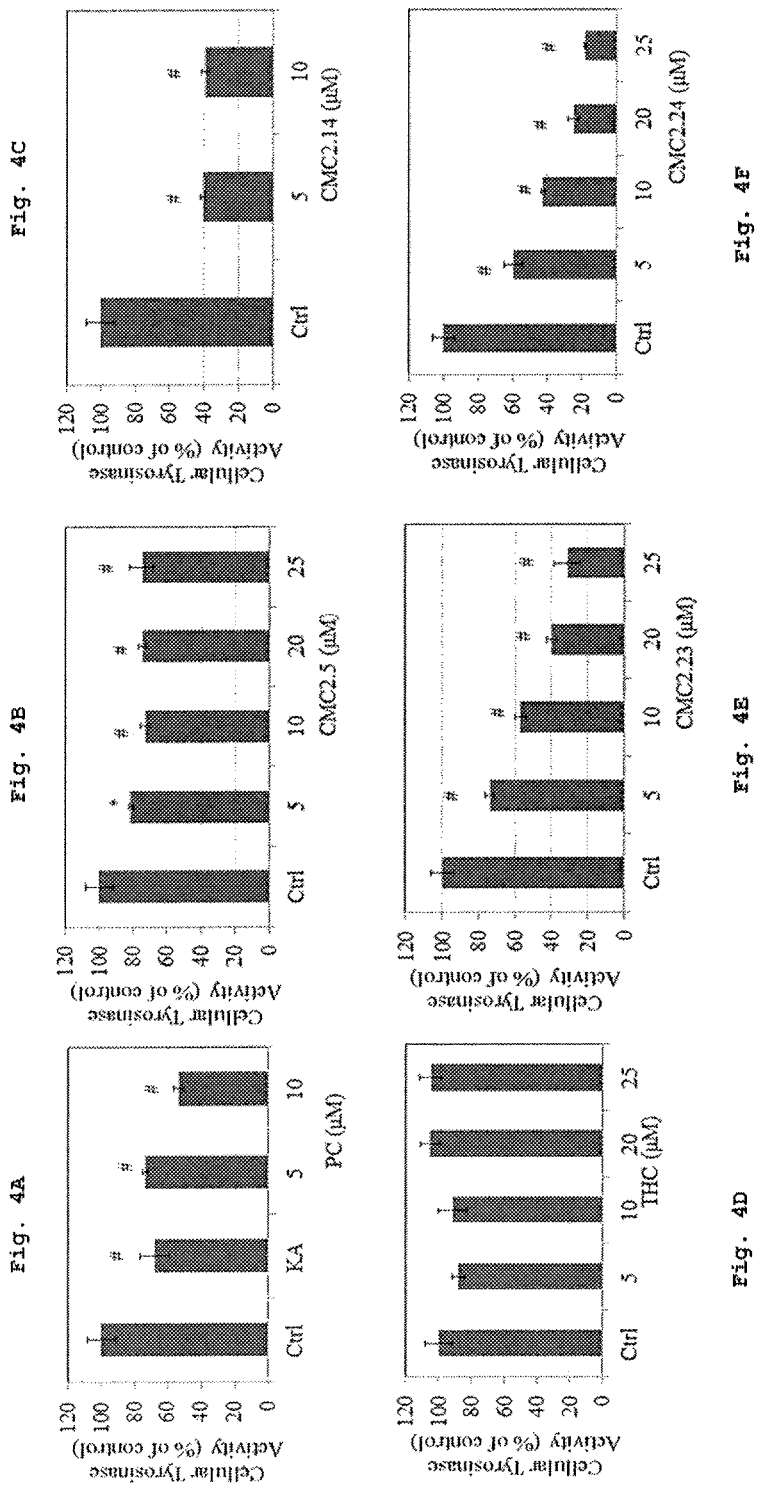
FIG. 4A: Cellular Tyrosinase activity in B16F10 cells treated for 48 hours with different concentrations of compounds; A) PC. KA (500 µM) was used as positive control. One-way ANOVA and Dunnett's post-hoc test. *-$p<0.01$ and #-$p<0.001$ vs. control One-way ANOVA with Dunnett's post-hoc test.
FIG. 4B: Cellular Tyrosinase activity in B16F10 cells treated for 48 hours with different concentrations of compounds; B) CMC2.14. KA (500 µM) was used as positive control. One-way ANOVA and Dunnett's post-hoc test. *-$p<0.01$ and #-$p<0.001$ vs. control One-way ANOVA with Dunnett's post-hoc test.
FIG. 4C: Cellular Tyrosinase activity in B16F10 cells treated for 48 hours with different concentrations of compounds; C) CMC2.24. KA (500 µM) was used as positive control. One-way ANOVA and Dunnett's post-hoc test. *-$p<0.01$ and #-$p<0.001$ vs. control One-way ANOVA with Dunnett's post-hoc test.
FIG. 4D: Cellular Tyrosinase activity in B16F10 cells treated for 48 hours with different concentrations of compounds; D) CMC2.5. KA (500 µM) was used as positive control. One-way ANOVA and Dunnett's post-hoc test. *-$p<0.01$ and #-$p<0.001$ vs. control One-way ANOVA with Dunnett's post-hoc test.
FIG. 4E: Cellular Tyrosinase activity in B16F10 cells treated for 48 hours with different concentrations of compounds; E) CMC2.23. KA (500 µM) was used as positive control. One-way ANOVA and Dunnett's post-hoc test. *-$p<0.01$ and #-$p<0.001$ vs. control One-way ANOVA with Dunnett's post-hoc test.
FIG. 4F: Cellular Tyrosinase activity in B16F10 cells treated for 48 hours with different concentrations of compounds; F) CMC2.24. KA (500 µM) was used as positive control. One-way ANOVA and Dunnett's post-hoc test. *-$p<0.01$ and #-$p<0.001$ vs. control One-way ANOVA with Dunnett's post-hoc test.

Example 5. Effect of Compounds on Intracellular Tyrosinase Activity in B16F10 Cells To identify the mechanism of depigmentation, we evaluated tyrosinase activity levels in B16F10 cellular lysates after treatment with the test compounds. FIG. 4 summarizes the results of PC, THC and CMCs on intracellular tyrosinase activity of B16F10 cells. The $IC_{50}$ values of cellular tyrosinase inhibition as well as melanin inhibition by CMCs are summarized in Table 1. The results demonstrate that CMCs inhibit melanogenesis in part by inhibiting intracellular tyrosinase activity: the order of inhibitory potency based on $IC_{50}$ is CMC2.14>CMC2.24>CMC2.23>CMC2.5.

TABLE 1

Summary of $IC_{50}$ values of melanin content inhibition and cellular tyrosinase inhibition in B16F10 cells exposed to PC and CMCs for 48 hours.*

| Compound | $IC_{50}$-Melanin Inhibition (µM) | $IC_{50}$-Cellular tyrosinase inhibition (µM) |
|---|---|---|
| PC | 20.83 | 12.57 |
| CMC2.14 | 15.08 | 4.69 |
| CMC2.5 | 28.33 | 50.71 |
| CMC2.23 | 24.14 | 12.97 |
| CMC2.24 | 18.07 | 6.92 |

*$IC_{50}$ values obtained by non-linear curve fitting in GraphPad.

Example 6. Effect of Compounds on Antioxidant Activity Via DPPH Assay

Figure 5A:
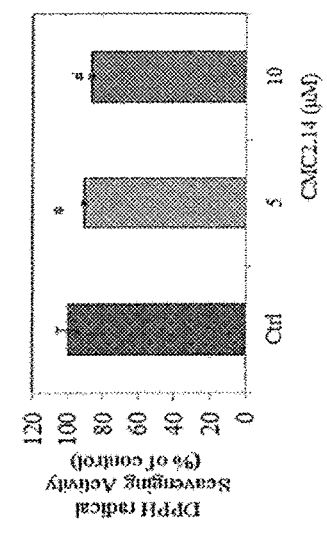
FIG. 5A: DPPH antioxidant activity estimated in cell-free system treated with different concentrations of CMCs derivatives; A) PC. #$p<0.01$ vs. control.
Figure 5B:
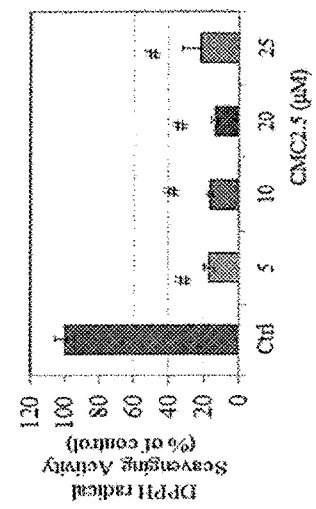
FIG. 5B: DPPH antioxidant activity estimated in cell-free system treated with different concentrations of CMCs derivatives; B) CMC2.5. #$p<0.01$ vs. control.
Figure 5C:
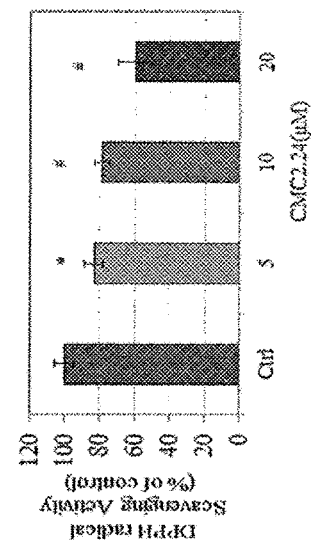
FIG. 5D: DPPH antioxidant activity estimated in cell-free system treated with different concentrations of CMCs derivatives; C) CMC2.14. #$p<0.01$ vs. control.
FIG. 5E: DPPH antioxidant activity estimated in cell-free system treated with different concentrations of CMCs derivatives; D) THC. #$p<0.01$ vs. control.
FIG. 5F: DPPH antioxidant activity estimated in cell-free system treated with different concentrations of CMCs derivatives; F) CMC2.24. #$p<0.01$ vs. control.
FIG. 5G: Cellular ROS estimated in B16F10 cells treated for 48 hours with different concentrations of compounds; G) PC. #$p<0.01$ vs. control. One-way ANOVA with Dunnett's test.
FIG. 5H: Cellular ROS estimated in B16F10 cells treated for 48 hours with different concentrations of compounds; H) CMC2.5. #$p<0.01$ vs. control. One-way ANOVA with Dunnett's test.
FIG. 5I: Cellular ROS estimated in B16F10 cells treated for 48 hours with different concentrations of compounds; I) CMC2.14. #$p<0.01$ vs. control. One-way ANOVA with Dunnett's test.
FIG. 5J: Cellular ROS estimated in B16F10 cells treated for 48 hours with different concentrations of compounds; J) THC. #$p<0.01$ vs. control. One-way ANOVA with Dunnett's test.
FIG. 5K: Cellular ROS estimated in B16F10 cells treated for 48 hours with different concentrations of compounds; K) CMC2.23. #$p<0.01$ vs. control. One-way ANOVA with Dunnett's test.
FIG. 5L: Cellular ROS estimated in B16F10 cells treated for 48 hours with different concentrations of compounds; L) CMC2.24. #$p<0.01$ vs. control. One-way ANOVA with Dunnett's test.
Figure 5D:
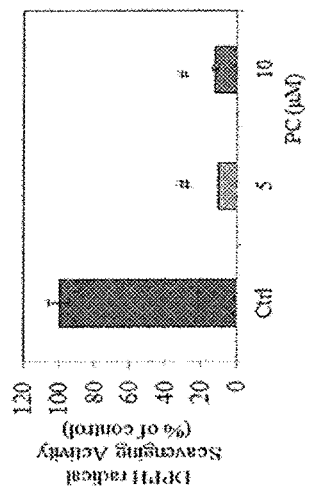
Figure 5E:
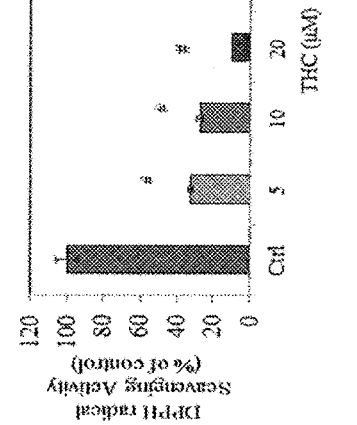
Figure 5I:
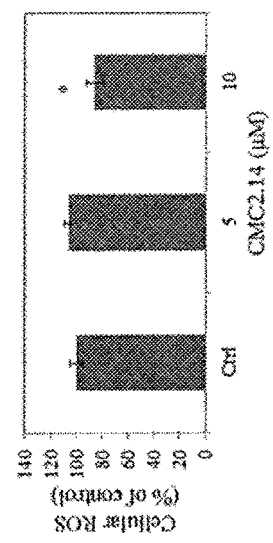

Antioxidant activity is desirable for compounds intend for use in diminishing pigmentation since excessive melanogenesis causes increased oxidative stress and generation of superoxide and hydrogen peroxide [Simon, J. D. et al. 2009]. The DPPH scavenging assay results for PC, THC and CMCs are summarized in FIG. 7. As expected, PC and THC showed significant antioxidant activity (FIGS. 5A and 5D), however, CMC2.24 and CMC2.14 did not demonstrate potent antioxidant activity (FIG. 5F, 5C) as compared to PC or THC using this assay. However, the other two CMCs—CMC2.5 and CMC2.23 showed significant DPPH radical scavenging activity (FIG. 5B, 5E). These results show that CMC2.24 and CMC2.14, which exhibited potent antimelanogenic activity earlier, might not depend upon free radical scavenging for their capaicty to inhibit melanin formation but rather may target other steps in melanogenesis. In contrast, CMC2.23 and CMC2.5 directly inhibit DPPH free radical which could be one of the mechanisms of inhibiting melanogenesis by these compounds. Both CMC2.23 and CMC2.5 possess the methoxy group on the two aryl rings, which confirms the importance of this group in DPPH antioxidant activity. This result is in agreement with a study where carbocyclic curcumin analogs were studied and the authors noted that electron withdrawing moieties compromise the antioxidant activity [Bhullar, K. S. et al. 2013].

Example 7. Effect of Compounds on Cellular ROS Levels

Figure 5H:
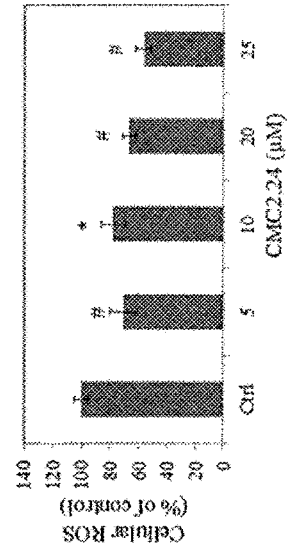
Figure 5G:
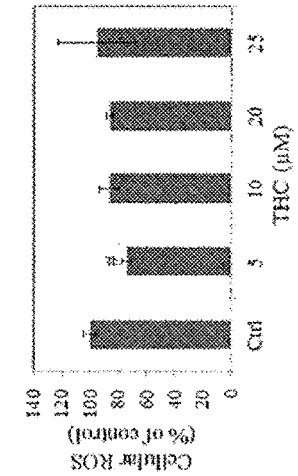
Figure 5L:
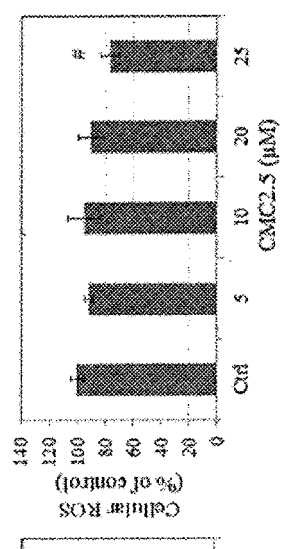
Figure 5K:
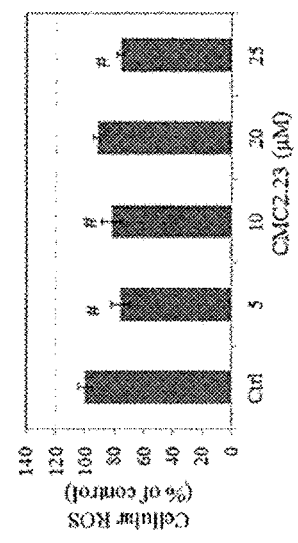
Figure 5J:
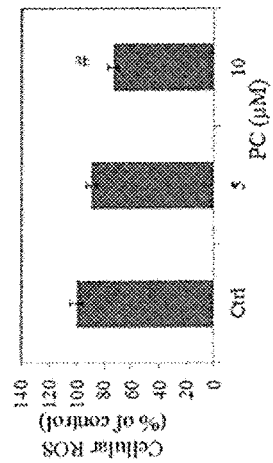

CMC2.24 showed the greatest antioxidant activity, reducing intracellular ROS in B16F10 cells by 40% at 20 µM (FIG. 5L). The effects of CMC2.24 and CMC2.14 at 10 µM were similar with both inhibiting cellular ROS levels up to 20%, similar to PC at 10 µM (inhibited 24%). CMC2.23 and CMC2.24 showed similar profiles at 5 and 10 µM. THC only showed significant inhibition of ROS levels of 24% at 5 µM while higher doses of THC were not significantly different from control (FIG. 5J). CMC2.5 only showed significant reduction at 25 µM with reduction of 23% (FIG. 5H).

Figure 6:
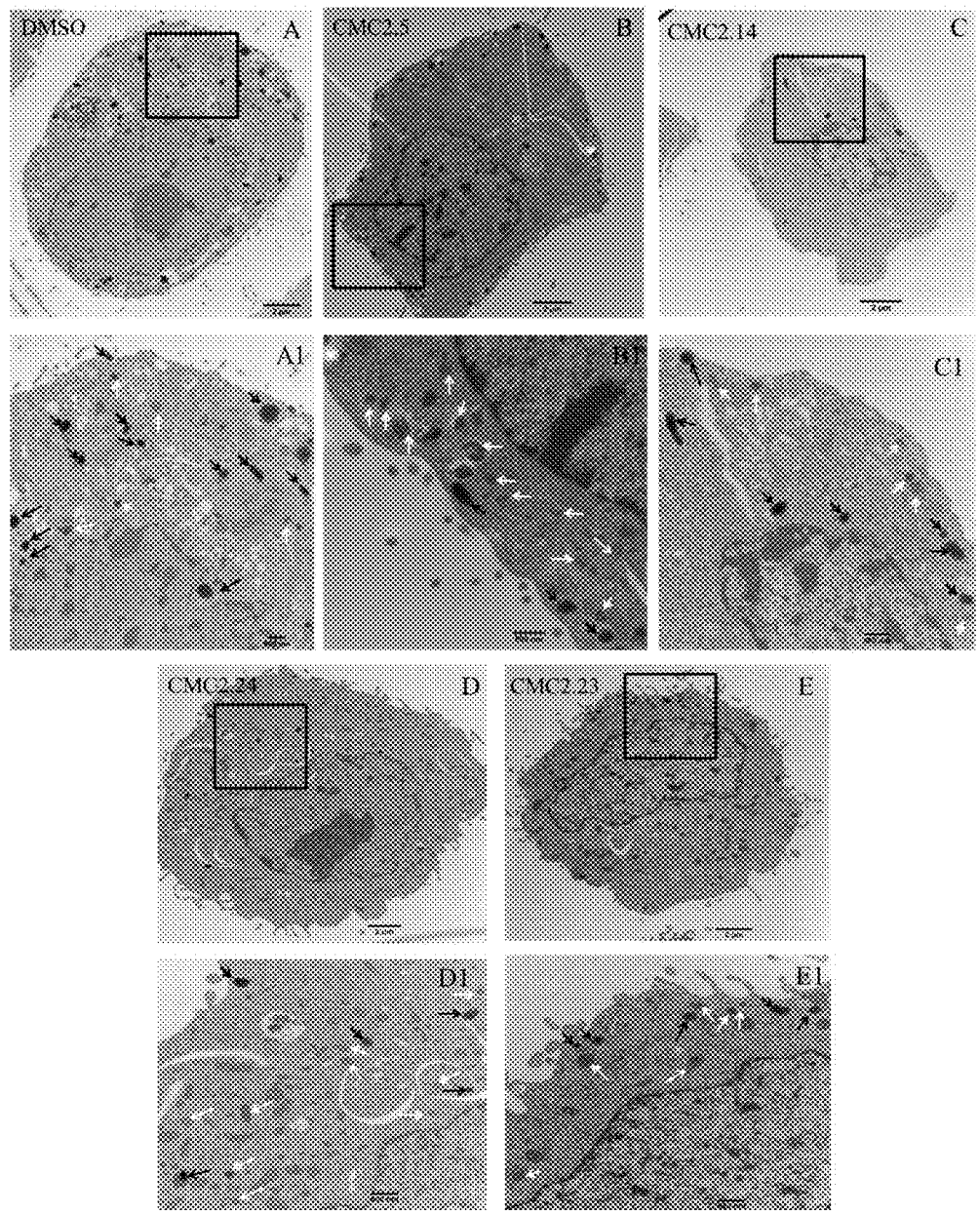
FIG. 6: Ultrastructural study of melanosome distribution in B16F10 cells treated for 48 hours with different concentrations of CMCs; A) DMSO control; B) CMC2.5; C) CMC2.14; D) 627 CMC2.24 and; E) CMC2.23; A1)-E1)

Example 8. Effects of Compounds on Ultrastructural Changes in Melanosome Distribution in B16F10 Cells We studied melanosome ultrastructure in B16F10 cells to qualitatively evaluate if the inhibitory mode of action of CMCs might encompass effect on melanosome maturation: previous studies have documented effects on maturation of melanosomes by antimelanogenic compounds [Bellei, B. et al. 2014; Liang, Y-R. et al. 2014; Wu, S-Y. et al. 2014]. Immature melanosomes are referred to as stage I+II while mature melanosomes are referred to as stage III+Stage IV. Control cells (FIGS. 6A and 6A1) had more mature melanosomes in cytoplasm, where they could be seen close to plasma membrane. In cells exposed to each of the CMCs tested (FIG. 6B-6E; 6B1-6E1), we noted greater densities of immature melanosomes. This is consistent with the hypothesis that these compounds inhibited melanin synthesis in part by arresting melanosome maturation, thus leading to and causing increase in immature melanosomes (stage III).

Example 9. Recovery Study of Tyrosinase Activity in B16F10 Cells

Normal melanin production is necessary for photo-protection and in immune regulation, and since tyrosinase is a key enzyme in melanogenesis pathway, skin lighteners which cause excessive or irreversible inhibition of tyrosinase activity could pose safety concerns. There have been reports in which recovery of tyrosinase activity in melanocytes has been studied by melanogenesis inhibitors [Charalambous, A. et al. 2015, Chawla, S. et al. 2008]. Hence, we evaluated CMCs for reversibility of tyrosinase activity inhibition using the highest concentrations for each of the CMCs. CMC2.14 at 10 µM caused loss of up to 75% of tyrosinase activity which was similar to CMC2.24 at 20 µM (FIG. 7). However, only after removal of CMC2.14 did we observe rapidrecovery of the tyrosinase activity in B16 mouse cells to 100%, while after removal of CMC2.24, B16 cells still retained only 28% of their original tyrosinase activity, significant from control, which could imply that a longer recovery period may be needed for cells to restore full tyrosinase activity from the higher concentration of 20 µM of CMC2.24. The higher concentrations of CMC2.23 (25 µM) and CMC2.24 (20 µM) may not be factors in causing delayed recovery, since after removal of 20 µM CMC2.5, B16 cells completely recovered their tyrosinase activity within 48 hours. This result might point to a structure-activity based effect on recovery of tyrosinase activity in which the methoxycarbonyl group modification of the β-diketone moiety of curcumin (as in CMC2.14 and CMC2.5) imparted a rapid reversible inhibition of tyrosinase activity, while the aminocarbonyl group modification (as in CMC2.24 and CMC2.23) imparted delayed reversible inhibition of tyrosinase activity. Longer recovery time points could not be tested using B16F10 cultures due to limitations caused by rapid cell growth and melanin production by B16 cultures, became resulting in the cultures becoming over-confluent and detached after longer periods of time.

Example 10. Effect of Compounds on MITF Protein Levels in B16F10 Cells

MITF is the master regulator of melanogenesis and a known transcription factor for tyrosinase gene. Downregulation of MITF is an attractive target for skin-whitening compounds. FIG. 8 shows results of MITF protein levels in B16F10 cells. PC at 10 µM inhibited upto 30% MITF expression level (p<0.01) compared to control. CMC2.14 did not show any significant reduction at tested concentrations (5-10 µM) while CMC2.5 significantly inhibited MITF protein levels by 35% at 20 M but did not show any suppression at 5 and 10 µM. However, CMC2.23 showed a potent inhibition of MITF at all tested concentrations and inhibited 20% at 5 M and a robust inhibition of 40% obtained at 20 and 25 µM. CMC2.24 exhibited a similar inhibitory profile like CMC2.23 at 25 µM with 40% attenuation of MITF protein levels. Taken together, the results demonstrate that CMCs affect melanogenesis by downregulating MITF protein levels.

Example 11. Effect of Compounds on Melanogenesis in αMSH-Stimulated B16F10 Cells In order to test if CMCs exhibited antimelanogenic activity in presence of hormone stimulation; we tested the compounds in presence of MSH and results are shown in FIG. 9. The cell pellets were darker with MSH stimulation and CMC 2.23 and 2.24 showed visible lightening. THC showed some reduction at 20 µM was still ineffective compared to similar concentrations of CMCs, Kojic acid, a positive control used at high concentration (500 µM) showed a marginal reduction of only 20%. Melanin was reduced by upto 50% at concentrations of 20 and 25 M for both CMC2.24 and CMC2.23. CMC2.5 showed a reduction of 36% and 42% at 20 and 25 M respectively (FIG. 9B). Overall, the results indicate that anti-melanogenic activity of CMC is independent of a pro-melanogenic stimulus since a similar inhibitory profile was obtained in basal (non-MSH stimulated) melanogenesis.

Example 12. Effect of Compounds on Keratinocyte and Fibroblast Viability by MTS Assay To establish safety for topical use in cosmetics, we evaluated cytotoxicity of the compounds in human keratinocyte and primary dermal human fibroblasts using MTS assay. PC was found to be significantly toxic in both HaCaT cells and NHDF cells. HaCaT cell viability was 90.12% at 10 µM (p<0.05) and reduced drastically at higher doses (FIG. 10A). NHDF viability was significantly low (71.9%) at 10 µM and was significantly reduced at higher concentrations (FIG. 10G). In the case of CMC2.14 both HaCaT and NHDF cell proliferation was significantly stimulated at 5 and 10 µM (23.2% and 15.5%), respectively, but was significantly toxic (p<0.01) at 20 and 25 µM (FIG. 10D). CMC2.5 was significantly toxic in HaCaT cells only at 25 µM and reduced cell growth by 15% (FIG. 10C) but was nontoxic in NHDF cells in the range 5-25 µM (FIG. 10I). CMC2.23 was nontoxic in the range for both HaCaT and NHDF cells and stimulated HaCaT cell proliferation by 11.3% at 10 µM and by 22.9% at 20 µM (FIG. 10E). CMC2.24 was nontoxic as well for the range tested (5-25 µM) in both cells and boosted cell HaCaT cell proliferation by 20% at 10 µM (p<0.01) (FIG. 10F).

Taken together, the results show that PC was the most toxic in both skin cells from 10 µM onwards, while both CMC2.23 and CMC2.24 were nontoxic in the concentration range 5-25 µM in both cells. CMC2.14 was a significant stimulator of cell proliferation in both cells, which may implicate a therapeutic effect of this compound in terms of providing benefits in wound healing and CMC2.5 at 25 µM showed some cytotoxicity to keratinocytes.

Example 13. Effect of Compounds on Phagocytosis of Fluosphere Beads by Keratinocytes Compounds which can inhibit uptake of melanin by keratinocytes can offer attractive target for skin pigmentation inhibitors at later stages in melanin pathway. We selected concentrations for the 4 CMCs which was nontoxic and potent in activity and the results of the phagocytosis assay are summarized in FIG. 11. All the 4 CMCs demonstrated similar levels of inhibition of bead uptake which was significantly reduced (p<0.01) as compared to control. CMC2.14 (10 µM) and CMC2.5 (20 µM) inhibited phagocytosis by 39.6% and 38.4%, respectively. CMC2.23 (20 µM) and CMC2.24 (20 µM) inhibited uptake by 37.4% and 34.4%, respectively.

Example 14. Effects of Compounds on Cytotoxicity in HEM-DP Cells by MTS Assay

PC, THC and CMCs (2.14, 2.24, 2.23 and 2.5) were screened for cytotoxicity in HEM-DP cells using MTS assay for duration of 48 hours. PC (5, 10 µM), CMC2.24 (5, 10 µM) and CMC2.23 (5, 10, 20 µM) were screened as nontoxic (FIG. 12A). Similarly, THC and CMC2.5 were also found to be nontoxic in all the concentration ranges tested: 5-25 µM (FIG. 12B; FIG. 12D). Unexpectedly, CMC2.14 was significantly toxic at 5 µM itself with viability of 84% and viability of 50% at 10 µM (FIG. 12C), hence was excluded in further testing on melanogenic activity.

Example 15. Effects of Compounds on Melanin Synthesis in HEM-DP Cells

FIG. 12G-H shows the results of melanin contents in HEM-DP cells treated with nontoxic concentrations of PC, THC and CMCs 424 (2.24, 2.23 and 2.5). CMC2.24 exhibited a reduction of up to 20% in melanin content compared to control, while PC at 5 and 10 µM did not show any significant difference vs. control (FIG. 12G). KA which was used as a positive control only showed 10% inhibition at much higher concentration (1 mM) compared to CMC2.24 at 10 µM. Both CMC2.23 and CMC2.5 showed similar anti-melanogenic activity profile (FIG. 12H) while THC did not show any inhibitory activity as expected. CMC2.23 inhibited melanin synthesis by 20% at both 10 and 20 µM and CMC2.5 exhibited similar inhibition activity.

Taken together, the results of CMCs on melanin production levels in HEM-DP cells suggest that PC and THC were inactive in concentration ranges tested for duration of 48 hours, while CMC2.24 was most potent by inhibiting 20% melanin production at 10 µM, while a similar inhibition rate could be achieved by both CMC2.23 and CMC2.5 at 20 µM. These results are in agreement with melanin inhibition activity obtained using B1610 mouse melanoma cells where CMC2.24 was most potent. Hence, in HEM-DP cells, the order of melanogenesis inhibitoryactivity is CMC2.24>CMC2.23=CMC2.5

Example 16. Effects of Compounds on Intracellular Tyrosinase Activity in HEM-DP Cells To explore mechanisms of melanogenesis inhibition in HEM-DP cells, intracellular tyrosinase activity was quantitated in cellular lysates after treatment with compounds for 48 hours. FIG. 13 shows the results of cellular tyrosinase activity study. KA was used at 1 mM as a positive control. Interestingly, PC significantly (p<0.01) inhibited cellular tyrosinase activity at 5 and 10 µM even though the cellular melanin levels as noted earlier were not different from control (FIG. 13A). Both CMC2.23 and CMC2.23 significantly (p<0.01) inhibited cellular tyrosinase activity at all tested concentrations. CMC2.24 at 5 and 10 µM inhibited tyrosinase activity by 30% and 41% respectively, whereas CMC2.23 at 5, 10 and 20 µM inhibited tyrosinase activity by 25%, 35% and 49% respectively (FIG. 13C). KA at 1 mM significantly inhibited only 20% of the activity. THC showed a dose-dependent reduction in cellular tyrosinase activity but significant inhibition of 24% was achieved at 25 µM (FIG. 13D). The results of PC and THC were unexpected since both compounds did not demonstrate any effect on melanin synthesis, but inhibited tyrosinase activity. CMC2.5 did not show potency at tyrosinase inhibition unlike CMC2.23 and CMC2.24 and tyrosinase activity was significantly inhibited by 16% only at 20 µM (FIG. 13E).

Overall, CMC2.5 and CMC2.23 both inhibited similar melanin levels at 20 µM as obtained before and the cellular tyrosinase data indicates that other mechanisms in melanogenesis pathway apart from tyrosinase enzyme pathway, could be at play in case of CMC2.5 since it only inhibited tyrosinase activity by 16% at 20 µM while CMC2.23 at similar concentration inhibited tyrosinase activity potently by 3-folds (49%).

Example 17. Recovery Study of Tyrosinase Activity in HEM-DP Cells

FIG. 14 shows results of intracellular tyrosinase activity recovery in HEM-DP after cessation of treatment with CMCs and cultured for 5 more days in media. Based on the results, HEM-DP cells partially recovered the tyrosinase activity after 5 days in case of exposure to CMC2.23 and CMC2.24 which showed similar trend in tyrosinase activity reduction and recovery. The tyrosinase activity on 5th day after removal was still significantly lower than control (p<0.01), which might normalize after extended recovery periods. CMC2.5 reduced tyrosinase activity by 12% at the exposure time, but levels did not reach statistical significance, but the levels were similar to controls after 5 days.

Example 18. Administration of the Compound to a Subject

An amount of compound CMC2.5, 2.23 or 2.24 is topically administered to a subject afflicted with hyperpigmentation. The amount of the compound is effective to treat the hyperpigmentation.

An amount of compound CMC2.5, 2.23 and 2.24 is topically administered to a subject in need of skin lightening. The amount of the compound is effective to lighten the skin of the subject.

DISCUSSION

Turmeric extract is comprised of three major curcuminoids (curcumin I, curcumin II and curcumin III), of which curcumin (curcumin I) is most abundant (77%), along with curcumin II (demethoxycurcumin, 17%) and curcumin III (bis-demethoxycurcumin, 3%) [Aggarwal, B. B. et al. 2007]. The commercial grade curcumin used in research studies is thus not chromatographically pure and usually consists of a mixture of curcumin I, II and III. Recently there have been several reports of melanogenesis inhibition by curcumin [Hosoya, T. et al. 2012; Jang, J. Y. et al. 2009; Lee, J. H. et al. 2010; Mustarichie, R. et al. 2013; Wolnicka-Glubisz, A. et al. 2015; Tu, C. X. et al. 2012]. However, the previous reports on curcumin as a melanogenesis inhibitor document use of curcumin preparations the source of which is inconsistent and variable. For example, studies which tested analogs of curcumins used curcumin from Sigma which has >80% curcumin that contains contaminating curcuminoids (II and III) while some studies did not even report the source of the curcumin preparation. Hence, a true comparison of structure-activity relation (SAR) cannot be made. Additionally, some studies have used alpha-melanocyte stimulating hormone (αMSH) or IBMX as an exogenous stimulator in cell culture studies to induce melanogenesis.

Tetrahydrocurcumin (THC), a colorless hydrogenated metabolite of yellow curcumin has been recently commercialized for treatment of cosmetic hyperpigmentation and is marketed as Sabiwhite™. THC has appeal for cosmetic sector as it does not have an intrinsic color unlike yellow curcumin [Arct, J. et al. 2014]. However, to date, no cell culture studies have been conducted with THC to assess its effects on melanogenesis and no comparisons with curcumin or its derivatives have been reported. CMC2.24, a triketonic N-phenylaminocarbonyl derivative of bis-45 demethoxycurcumin, exhibits enhanced stability and solubility compared to curcumin and also demonstrated diverse potential pharmacological activities such as treatment of anthrax by inhibiting lethal factor enzyme [Antonelli, A. C. et al. 2014], treatment of prostate cancer [Botchkina, et al. 2013], normalizing wound healing in diabetes in rats [Zhang, Y. et al. 2016] and reduction of periodontitis in rats [Elburki, M. S. et al. 2014]. CMC2.5 (4-methoxycarbonyl curcumin), another derivative, has also demonstrated performance superior to that of the parent compound (curcumin) in treatment of inflammation in periodontitis [Gu, Y. et al. 2013]. The synthesis scheme for other CMCs which are based on the Pabon reaction has been summarized in previous report [Zhang, Y. et al. 2012].

In the present work, four CMCs (referred as CMC2.14, CMC2.5, CMC2.24 and CMC2.23) can be grouped into two categories which differ in the i) type of substituent on the β-diketone (—COOCH$_3$ and —CONHPh), and ii) presence or absence of the methoxy group on the aryl rings All four CMCs were tested for inhibition of melanogenesis. Sabiwhite™ (tetrahydrocurcumin, referred as THC hereafter) was also used to compare alongside curcumin and CMCs to evaluate whether CMCs at low doses could have greater potential as antimelanogenic agents than white THC for cosmetic purposes. Moreover, to date, there is no study which has explored if the double bond conjugation in curcumin is unique in terms of melanogenesis inhibitory activity Hence testing both PC (curcumin) and THC (tetrahydrocurcumin) can help in dissecting the role of the double-bond conjugation in modulating melanin inhibition. The SAR study focused on evaluating the three regions of the parent curcumin structural skeleton—i) THC as a model for effects of hydrogenation of the two double bonds bridging the phenyl rings to the central β-diketone moiety; ii) CMC2.5 and CMC2.14 as models for effects of substituents on the two phenyl rings (—OCH$_3$ and —H) and; iii) CMC2.23 and CMC2.24 as models for modification of the central β-diketone moiety (—COOCH$_3$ and —CONHPh).

The results provide for the novel use of the CMCs (CMC2.5, CMC2.24 and CMC2.23) for skin depigmentation, which are far superior to the colored parent compound (curcumin) and the white curcumin (THC, Sabiwhite™). At low micro-molar ranges tested in 5-25 µM, the synthetic CMCs (CMC2.24, CMC2.23 and CMC2.5) were superior inhibitors of melanogenesis compared to both PC and THC, both of which were inactive as inhibitors of melanogenesis at similar doses when tested in primary human melanocytes (in addition, PC is highly toxic to human dermal fibroblasts and the HaCaT human keratinocyte line). Also, the color of CMCs at such low doses should not hinder their use in cosmetic formulations.

The mechanisms of action of the CMCs include direct inhibitory effects on tyrosinase enzyme activity (and at the cellular levels of enzyme protein), which is mostly or completely reversible upon removal of the compounds, antioxidant activity, suppression of MITF protein levels, inhibition of melanosome maturation and melanosome transport to keratinocytes. Additionally, since CMC2.24 is being pursued as a pharmacological candidate for treatment interventions for canine periodontitis, it holds potential for use in clinical settings to treat hyperpigmentation disorders in dark skinned individuals as its preclinical safety and toxicology studies have already been undertaken in preparation for future clinical trials. Hence, CMC2.24, as well as CMC2.5 and CMC2.23 and derivatives thereof, could be repurposed as drugs for treating hyperpigmentation disorders in dermatology.

REFERENCES

Aggarwal B E, et al. (2007) Curcumin: the Indian solid gold. Adv Exp Med Biol 595: 1-75.

Ammon H. P. T.; Wahl M. A. (1991) Pharmacology of *Curcuma longa*. Planta Med, 57, 1-7.

Ando H, et al. (2012) Melanosomes are transferred from melanocytes to keratinocytes through the processes of packaging, release, uptake, and dispersion. Journal of Investigative Dermatology 132: 1222-1229.

Antonelli A C, et al. (2014) Inhibition of anthrax lethal factor by curcumin and chemically modified curcumin derivatives. Journal of enzyme inhibition and medicinal chemistry 29: 663-669.

Arct J, et al. (2014) Evaluation of skin colouring properties of *curcuma longa* extract. Indian J Pharm Sci 76: 374-378.

Baek S-H, et al. (2015) Cellular anti-melanogenic effects of a *Euryale ferox* seed extract ethyl acetate fraction via the lysosomal degradation machinery. International journal of molecular sciences 16: 9217-9235.

Bellei B, et al. (2014) Pyridinyl imidazole compounds interfere with melanosomes sorting through the inhibition of Cyclin G-associated Kinase, a regulator of cathepsins maturation. Cellular signalling 26: 716-723.

Bhullar K S, et al. (2013) Curcumin and its carbocyclic analogs: structure-activity in relation to antioxidant and selected biological properties. Molecules 18: 566 5389-5404.

Botchkina G I, et al. (2013) Prostate cancer stem cell-targeted efficacy of a new-generation taxoid, SBT-1214 and novel polyenolic zinc-binding curcuminoid, CMC2.24. PloS one 8: e69884.

Cardinali G, et al. (2008) Melanosome transfer promoted by keratinocyte growth factor in light and dark skin-derived keratinocytes. J Invest Dermatol 128: 558-567.

Cardinali G, et al. (2005) Keratinocyte growth factor promotes melanosome transfer to keratinocytes. J Invest Dermatol 125: 1190-1199.

Chang T S (2009) An updated review of tyrosinase inhibitors. Int J Mol Sci 10: 2440-2475.

Charalambous A, et al. (2015) 1, 2, 3-Dithiazoles-new reversible melanin synthesis inhibitors: a chemical genomics study. 578 MedChemComm 6: 935-946.

Chawla S, et al. (2008) Mechanism of tyrosinase inhibition by deoxyArbutin and its second-generation derivatives. Br J Dermatol 159: 1267-1274.

Cheng S L, et al. (2007) Toxicogenomics of A375 human malignant melanoma cells treated with arbutin. J Biomed Sci 14: 87-105.

Cichorek M, et al. (2013) Skin melanocytes: biology and development. Postepy Dermatol Alergol 30: 30-41.

Elburki M S, et al. (2014) A novel chemically modified curcumin reduces severity of experimental periodontal disease in rats: initial observations. Mediators Inflamm 2014: 959471.

Esatbeyoglu T, et al. (2012) Curcumin—from molecule to biological function. Angew Chem Int Ed Engl 51: 5308-5332.

Fitzpatrick T B, Breathnach A S (1963) [the Epidermal Melanin Unit System]. Dermatol Wochenschr 147: 481-489.

García-Gavín J, et al. (2010) Pigmented contact dermatitis due to kojic acid. A paradoxical side effect of a skin lightener. Contact Dermatitis 62: 63-64.

Gu Y, et al. (2013) 4-methoxycarbonyl curcumin: a unique inhibitor of both inflammatory mediators and periodontal inflammation. Mediators of inflammation 2013.

Gupta S. C. et al. (2011) Multitargeting by curcumin as revealed by molecular interaction studies. Natural Products Reports, 28, 1937-1955.

Hosoya T, et al. (2012) Curcumin-like diarylpentanoid analogues as melanogenesis inhibitors. Journal of Natural Medicines 66: 166-176.

Jang J Y, et al. (2009) Partially purified Curcuma longa inhibits alpha-melanocyte-stimulating hormone-stimulated melanogenesis through extracellular signal-regulated kinase or Akt activation-mediated signalling in B16F10 cells. Exp Dermatol 18: 689-694.

Kooyers T, Westerhof W (2006) Toxicology and health risks of hydroquinone in skin lightening formulations. Journal of the European academy of Dermatology and Venereology 20: 777-780.

Lee J H, et al. (2010) Curcumin suppresses alpha-melanocyte stimulating hormone-stimulated melanogenesis in B16F10 cells. International Journal of Molecular Medicine 26: 101-106.

Liang Y-R, et al. (2014) Inhibitory effects of (-)-epigallocatechin-3-gallate on melanogenesis in ultraviolet A-induced B16 murine melanoma cell. Tropical Journal of Pharmaceutical Research 13: 1825-1831.

Mustarichie R. et al. (2013) In-Silico Study of Curcumin, Demethoxycurcumin and Xanthorrizol As Skin Whitening Agents. World Journal of Pharmaceutical Sciences, 1(3), 72-80.

Simon J D, et al. (2009) Current challenges in understanding melanogenesis: bridging chemistry, biological control, morphology, and function. Pigment Cell Melanoma Res 563 22: 563-579.

Tu C X, et al. (2012) Curcumin inhibits melanogenesis in human melanocytes. Phytother Res 26: 174-179.

Wolnicka-Glubisz A, et al. (2015) Curcumin does not switch melanin synthesis towards pheomelanin in B16F10 cells. Archives of dermatological research 307: 89-98.

Wu S-Y S, et al. (2015) 4-(Phenylsulfanyl) butan-2-One Suppresses Melanin Synthesis and Melanosome Maturation In Vitro and In Vivo. International journal of molecular sciences 16: 20240-20257.

Zhang Y. et al. (2012) pKa, Zinc- and Serum Albumin-Binding of Curcumin and Two Novel Biologically-Active, Chemically-Modified Curcumins. Current Medicinal Chemistry, 19(25), 4367-4375.

Zhang Y. et al. (2012) Design, Synthesis, and Biological Activity of New Polyenolic Inhibitors of Matrix Metalloproteinases: A Focus on Chemically-Modified Curcumins. Current Medicinal Chemistry, 19(25), 4348-4358.

Zhang Y, et al. (2016) A novel chemically modified curcumin "normalizes" wound-healing in rats with experimentally induced type I diabetes: initial studies. Journal of diabetes research 2016.

What is claimed is:

1. A method of treating a subject afflicted with hyperpigmentation comprising topically administering to the subject in need of such treatment an effective amount of a compound having the structure:

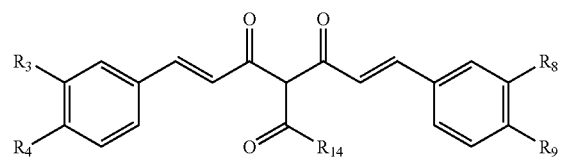

wherein
$R_3$, $R_4$, $R_8$ and $R_9$ are each independently, H or —$OR_{28}$;
wherein $R_{28}$ is H or $C_{1-10}$ alkyl; and
$R_{14}$ is —$NR_{16}R_{17}$,
wherein $R_{16}$ and $R_{17}$ are each, independently, H or aryl;
wherein the aryl is a phenyl;
wherein each occurrence of alkyl is unsubstituted, or a salt or ester thereof, so as to thereby treat the subject.

2. The method of claim 1, wherein the compound reduces melanin synthesis in the subject.

3. The method of claim 1, wherein the compound inhibits melanogenesis in the subject.

4. The method of claim 1, wherein the compound inhibits tyrosinase activity in the subject.

5. The method of claim 1, wherein the compound lightens the skin tone of the subject relative to the subject's natural skin tone.

6. The method of claim 1, wherein $R_3$, $R_4$, $R_8$, and $R_9$ are each, independently, H, —$OCH_3$, or —OH.

7. The method of claim 1, wherein the compound has the structure:

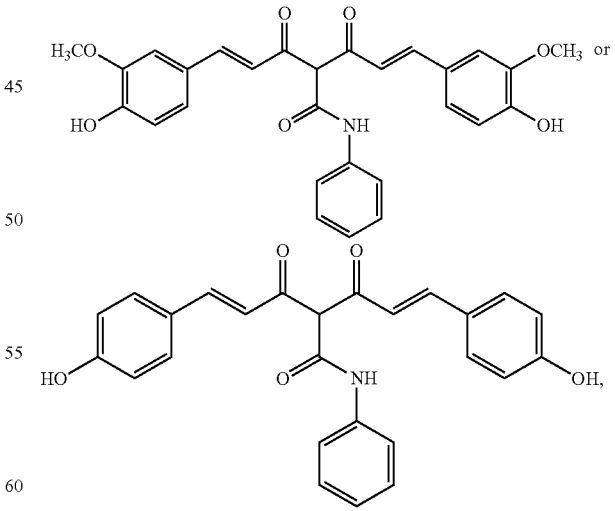

or a salt thereof.

8. A method of lightening the skin tone of a subject comprising topically administering to the subject in need of such treatment an effective amount of a compound having the structure:

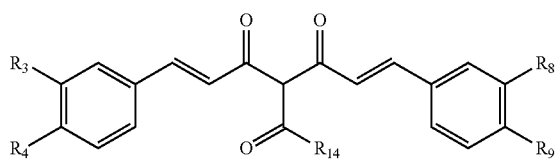

wherein $R_3$, $R_4$, $R_8$ and $R_9$ are each independently, H or —$OR_{28}$;
    wherein $R_{28}$ is H or $C_{1-10}$ alkyl; and $R_{14}$ is —$NR_{16}R_{17}$,
    wherein $R_{16}$ and $R_{17}$ are each, independently, H or aryl;
        wherein the aryl is a phenyl;
    wherein each occurrence of alkyl is unsubstituted, or a salt or ester thereof, so as to thereby treat the subject.

9. The method of claim 8, wherein the compound reduces melanin synthesis in the subject.

10. The method of claim 8, wherein the compound inhibits melanogenesis in the subject.

11. The method of claim 8, wherein the compound inhibits tyrosinase activity in the subject.

12. The method of claim 8, wherein the compound lightens the skin tone of the subject relative to the subject's natural skin tone.

13. The method of claim 8, wherein $R_3$, $R_4$, $R_8$, and $R_9$ are each, independently, H, —$OCH_3$, or —OH.

14. The method of claim 8, wherein the compound has the structure:

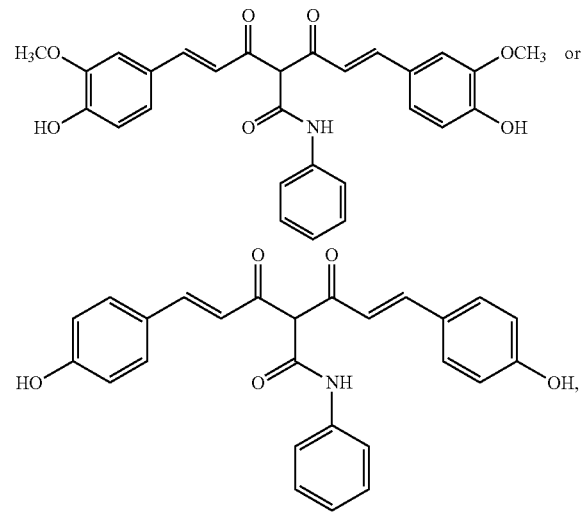

or a salt thereof.

15. A method of inhibiting melanogenesis for reducing skin melanin levels in a subject comprising topically administering to the subject in need of such treatment an effective amount of a compound having the structure:

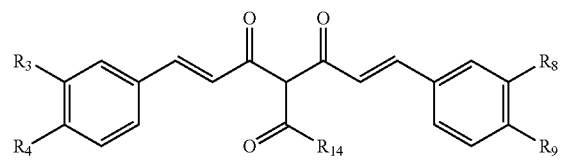

wherein $R_3$, $R_4$, $R_8$ and $R_9$ are each independently, H or –$OR_{28}$;
    wherein $R_{28}$ is H or $C_{1-10}$ alkyl; and $R_{14}$ is —$NR_{16}R_{17}$,
    wherein $R_{16}$ and $R_{17}$ are each, independently, H or aryl;
        wherein the aryl is a phenyl;
    wherein each occurrence of alkyl is unsubstituted, or a salt or ester thereof, so as to thereby treat the subject.

16. The method of claim 15, wherein $R_3$, $R_4$, $R_8$, and $R_9$ are each, independently, H, —$OCH_3$, or —OH.

17. The method of claim 15, wherein the compound has the structure:

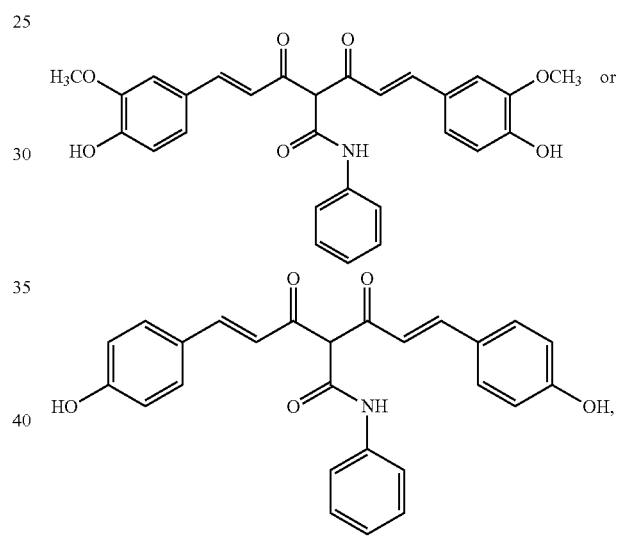

or a salt thereof.

18. The method of claim 15, wherein the compound reduces melanin synthesis in the subject.

19. The method of claim 15, wherein the compound inhibits tyrosinase activity in the subject.

20. The method of claim 15, wherein the compound lightens the skin tone of the subject relative to the subject's natural skin tone.

\* \* \* \* \*